United States Patent
Luschtinetz et al.

(10) Patent No.: US 12,035,622 B2
(45) Date of Patent: Jul. 9, 2024

(54) TRIAZINE COMPOUND AND ORGANIC SEMICONDUCTNG LAYER COMPRISING THE SAME

(71) Applicant: Novaled GmbH, Dresden (DE)

(72) Inventors: Regina Luschtinetz, Dresden (DE); Domagoj Pavicic, Dresden (DE); Benjamin Schulze, Dresden (DE)

(73) Assignee: Novaled GmbH, Dresden (DE)

( * ) Notice: Subject to any disclaimer, the term of this patent is extended or adjusted under 35 U.S.C. 154(b) by 388 days.

(21) Appl. No.: 16/761,401

(22) PCT Filed: Nov. 1, 2018

(86) PCT No.: PCT/EP2018/079925
§ 371 (c)(1),
(2) Date: May 4, 2020

(87) PCT Pub. No.: WO2019/086568
PCT Pub. Date: May 9, 2019

(65) Prior Publication Data
US 2020/0365810 A1    Nov. 19, 2020

(30) Foreign Application Priority Data
Nov. 6, 2017  (EP) ..................... 17200125

(51) Int. Cl.
| C07D 251/24 | (2006.01) |
| C07D 401/10 | (2006.01) |
| H10K 50/165 | (2023.01) |
| H10K 85/60  | (2023.01) |

(52) U.S. Cl.
CPC ......... H10K 85/654 (2023.02); C07D 251/24 (2013.01); C07D 401/10 (2013.01); H10K 85/615 (2023.02); *H10K 50/165* (2023.02)

(58) Field of Classification Search
CPC .. H10K 85/654; H10K 85/615; H10K 50/165; H10K 2102/3026; C07D 251/10; C07D 401/10
See application file for complete search history.

(56) References Cited

U.S. PATENT DOCUMENTS

| 8,765,270  | B2* | 7/2014  | Sekiguchi ........... H01L 51/0067 |
|            |     |         | 428/917 |
| 10,068,948 | B2  | 9/2018  | Yun et al. |
| 10,093,852 | B2  | 10/2018 | Huh et al. |
| 10,468,605 | B2* | 11/2019 | Yoon ................... H10K 85/622 |
| 10,580,994 | B2* | 3/2020  | Kim .................... H01L 51/0052 |
| 2012/0217449 | A1 | 8/2012  | Spreitzer et al. |
| 2014/0374713 | A1 | 12/2014 | Cho et al. |
| 2016/0079546 | A1 | 3/2016  | Park et al. |
| 2016/0233434 | A1 | 8/2016  | Jeong et al. |
| 2016/0276597 | A1 | 9/2016  | Lee et al. |
| 2019/0263834 | A1 | 8/2019  | Jeong et al. |
| 2019/0378996 | A1 | 12/2019 | Stoessel et al. |
| 2020/0058879 | A1 | 2/2020  | Takahashi et al. |
| 2020/0095269 | A1 | 3/2020  | Luschtinetz et al. |

FOREIGN PATENT DOCUMENTS

| CN | 103187531 A  | 7/2013  |
| CN | 105461685 A  | 4/2016  |
| CN | 106749234 A  | 5/2017  |
| CN | 106803539 A  | 6/2017  |
| EP | 2055704 A1   | 5/2009  |
| EP | 3301093 A1   | 4/2018  |
| JP | 2012082136 A | 4/2012  |
| JP | 2017105717 A | 6/2017  |
| KR | 20160150185 A | 12/2016 |
| KR | 20180035359 A | 4/2018  |
| WO | 2010/067894 A1 | 6/2010 |
| WO | 2016/052819 A1 | 4/2016 |

OTHER PUBLICATIONS

RN2055648-93-4, registry database compound, Jan. 9, 2017.*
PCT International Search Report and Written Opinion for PCT Application No. PCT/EP2018/077925 dated Dec. 13, 2018 (16 pages).
European Office Action for EP Application No. 17200125.7 dated Jan. 2, 2020 (4 pages).

(Continued)

*Primary Examiner* — Sun Jae Yoo

(74) *Attorney, Agent, or Firm* — Eversheds Sutherland (US) LLP

(57) ABSTRACT

The present invention relates to a compound represented by the general formula (I): (formula I) an organic semiconducting layer comprising the compound, an organic electronic device comprising the organic semiconducting layer and a device comprising the organic electronic device.

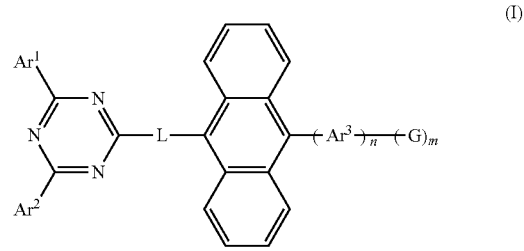

12 Claims, 2 Drawing Sheets

(56) References Cited

OTHER PUBLICATIONS

European Search Report for EP Application No. 20200666.4 dated Dec. 17, 2020 (7 pages).
Kim et al., "Highly efficient non-doped deep blue fluorescent emitters with horizontal emitting dipoles using interconnecting units between chromophores," Chemical Communications, 2016, 52(73):10956-10959.
Communication Pursuant to Article 94(3) of European Patent Office for EP Application No. 20 2020 666.4; dated Nov. 12, 2021.
Notification of First Office Action issued in China application No. 201880070647.8, dated Oct. 10, 2022, 13 pages.
Notice to File a Response issued in Korean application No. 10-2020-7016114, dated Apr. 5, 2023, 9 pages.
Notice to File a Response issued in corresponding Korean application number 10-2024-7003882, dated Apr. 19, 2024 (11 pages).

\* cited by examiner

TRIAZINE COMPOUND AND ORGANIC SEMICONDUCTNG LAYER COMPRISING THE SAME

CROSS REFERENCE TO RELATED APPLICATIONS

This application is a U.S. national phase application of PCT/EP2018/079925, filed Nov. 1, 2018, which claims priority to European Patent Application No. 17200125.7, filed Nov. 6, 2017. The content of these applications is incorporated herein by reference.

The present invention relates to a compound, an organic semiconducting layer comprising the same, an organic electronic device comprising the organic semiconducting layer, and a device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

WO 2016/171406 A2 discloses an organic light-emitting device comprising triazine compounds with both pyridine and cyano groups. However, the disclosed materials show rather low glass transition temperatures. Furthermore, devices comprising such compounds need high driving voltages and show rather low current efficiencies.

It is, therefore, an object of the present invention to provide novel compounds for use in the layers of organic electronic devices overcoming drawbacks of the prior art, in particular compounds which are suitable to improve the performance of the organic electronic devices. In particular, it is the object of the present invention to improve current efficiencies of OLED devices and the glass transition temperatures of compounds for use therein. Furthermore, it is an object of the present invention to provide compounds suitable to reduce the driving voltage of an organic electronic device comprising the same.

DESCRIPTION OF THE INVENTION

The above object is achieved by a compound represented by the general formula (I)

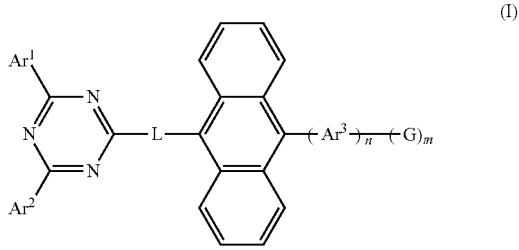

(I)

wherein $Ar^1$ and $Ar^2$ are independently selected from the group consisting of substituted or unsubstituted $C_6$ to $C_{60}$ aryl and substituted or unsubstituted $C_2$ to $C_{60}$ heteroaryl, wherein the substituents, if present in the respective aryl or heteroaryl group, are independently selected from the group consisting of $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched fluorinated cyclic alkyl, $C_3$-$C_{12}$ fluorinated cyclic alkyl, $C_3$-$C_{12}$ fluorinated cyclic alkoxy; CN; $C_2$-$C_{20}$ heteroaryl, OR, SR, (C=O)R, (C=O)NR$_2$, SiR$_3$, (S=O)R, (S=O)$_2$R, $C_{12}$-$C_{40}$ aryl phosphine oxide, $C_7$-$C_{40}$ aryl-alkyl-phosphine oxide;

$Ar^3$ is selected from the group consisting of substituted or unsubstituted $C_6$ to $C_{60}$ arylene and substituted or unsubstituted $C_2$ to $C_{60}$ heteroarylene, wherein the substitutents, if present in the respective arylene or heteroarylene group, are independently selected from the group consisting of $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_3$-$C_{12}$ alkoxy; $C_3$-$C_{12}$ branched fluorinated cyclic alkyl, $C_3$-$C_{12}$ fluorinated cyclic alkyl, $C_3$-$C_{12}$ fluorinated cyclic alkoxy; CN; $C_2$-$C_{20}$ heteroaryl, OR, SR, (C=O)R, (C=O)NR$_2$, SiR$_3$, (S=O)R, (S=O)$_2$R, $C_{12}$-$C_{40}$ aryl phosphine oxide, $C_7$-$C_{40}$ aryl-alkyl-phosphine oxide;

L represents a single bond or is selected from $C_6$ to $C_{60}$ arylene;

n is 0 or 1;

m is an integer from 1 to 3;

G is selected from the group consisting of H, substituted or unsubstituted $C_2$ to $C_{60}$ heteroaryl and substituted $C_6$ to $C_{60}$ aryl, wherein the substituents, if present in the respective aryl or heteroaryl group, are independently selected from the group consisting of $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched cyclic fluorinated alkyl, $C_3$-$C_{12}$ cyclic fluorinated alkyl, $C_3$-$C_{12}$ cyclic fluorinated alkoxy; CN; $C_2$-$C_{20}$ heteroaryl OR, SR, (C=O) R, (C=O)NR$_2$, SiR$_3$, (S=O)R, (S=O)$_2$R, $C_{12}$-$C_{40}$ aryl phosphine oxide, $C_7$-$C_{40}$ aryl-alkyl-phosphine oxide; and R is independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

Surprisingly, it has been found by the present inventors that the combination of triazine moiety with an anthracene moiety yields significantly increased glass transition temperatures of respective compounds by several 10K.

With respect to $Ar^1$ and $Ar^2$ the substituents, as present in the respective aryl or heteroaryl group, may be selected from the group consisting of diarylphosphine oxide, $C_2$ to $C_2$ heteroaryl, fluorinated $C_1$ to $C_6$ alkyl, and fluorinated $C_1$ to $C_6$ alkoxy.

With respect to $Ar^3$, the substituents, if present in the respective arylene or heteroarylene group, may independently is selected from the group consisting of diarylphosphine oxide, $C_2$ to $C_{20}$ heteroaryl, fluorinated $C_1$ to $C_6$ alkyl and fluorinated $C_1$ to $C_6$ alkoxy.

With respect to G, the substituents, if present in the respective aryl or heteroaryl group, may independently be selected from the group consisting of diarylphosphine oxide, $C_2$ to $C_{20}$ hetaryl, fluorinated $C_1$ to $C_6$ alkyl, fluorinated $C_1$ to $C_6$ alkoxy and CN.

$Ar^1$ and $Ar^2$ may be independently selected from unsubstituted $C_6$ to $C_{60}$ aryl or unsubstituted $C_2$ to $C_{60}$ heteroaryl. $Ar^1$ and $Ar^2$ may be independently selected from $C_6$ to $C_{12}$ aryl. $Ar^1$ and $Ar^2$ may be both selected as phenyl. Respective choices allow fine tuning of the electronic structure of the inventive compound to improve the usability of the inventive compounds in organic semiconducting layers of organic electronic devices.

The group $Ar^3$ may be present in the compound represented by the general formula (I), corresponding to n=1, or may not be present in the compound represented by the general formula (I), corresponding to n=0. In the inventive compound represented by the general formula (I) n may be 0. $Ar^3$, if present, may be selected from substituted or unsubstituted $C_6$ to $C_{60}$ arylene with the substituents, if present in the respective group, as defined as above. $Ar^3$ may be selected from $C_6$ to $C_{12}$ arylene. $Ar^3$ may be selected as phenylene. Respective choices allow fine tuning of the electronic structure of the inventive compound to improve the usability of the inventive compounds in organic semiconducting layers of organic electronic devices.

L may represent a single bond or may be substituted or unsubstituted $C_6$ arylene. In this regard, the substituents, if present in the respective L, are as defined above. L may be phenylene. L may be meta-phenylene, i.e. the triazine moiety and the anthracenylene moiety are in meta-position with respect to each other. L may be para-phenylene, i.e. the triazine moiety and the anthracenylene moiety are arranged in para-position with respect to each other. Respective choices allow fine tuning of the electronic structure of the inventive compound to improve the usability of the inventive compounds in organic semiconducting layers of organic electronic devices.

G may be selected from the group consisting of $C_2$ to $C_{20}$ heteroaryl and CN. G may be selected from the group consisting of nitrogen-containing $C_2$ to $C_{20}$ heteroaryl and CN. G may be selected from the group consisting of pyridinyl and CN. Respective choices allow fine tuning of the electronic structure of the inventive compound to improve the usability of the inventive compounds in organic semiconducting layers of organic electronic devices.

With respect to the compound represented by the general formula (I) it may be provided that if n=0 then L is selected from $C_6$ to $C_{60}$ arylene.

The compound represented by general formula (I) may be a compound wherein $Ar^1$ and $Ar^2$ are independently selected from unsubstituted $C_6$ to $C_{42}$ aryl or $C_2$-$C_{42}$ heteroaryl; Ara is selected from unsubstituted $C_6$ to $C_{42}$ arylene or $C_2$ to $C_{42}$ heteroarylene; L represents a single bond or is $C_6$ to $C_{42}$ aryl; G is selected from the group consisting of H, N-containing heteroaryl and CN; n is 0 or 1; and m is 1. Respective choices allow fine tuning of the electronic structure of the inventive compound to improve the usability of the inventive compound in organic semiconducting layers of organic electronic devices.

In this regard, $Ar^1$ and $Ar^2$ may be independently selected from phenyl, biphenyl, naphtyl, dibenzofuranyl, fluorenyl, dibenzothienyl; $Ar^3$, if present, may be phenyl or may be absent (n=0); L may represent a single bond or is phenyl; and G may be H, pyridinyl or CN. Respective choices allow fine tuning of the electronic structure of the inventive compound to improve the usability of the inventive compounds in organic semiconducting layers of organic electronic devices.

The compound represented by general formula (I) may be represented by one of the following formulas A to M

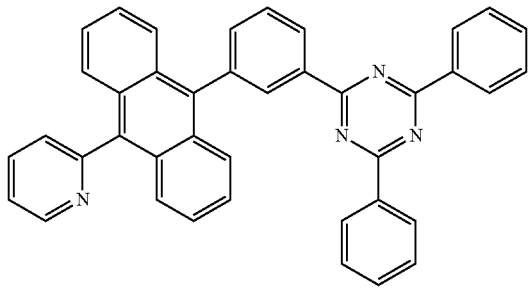

(A)

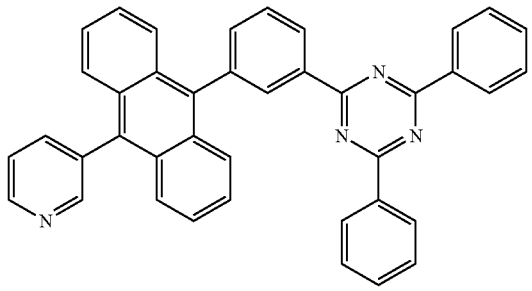

(B)

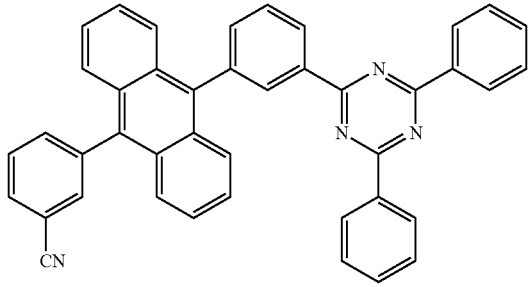

(C)

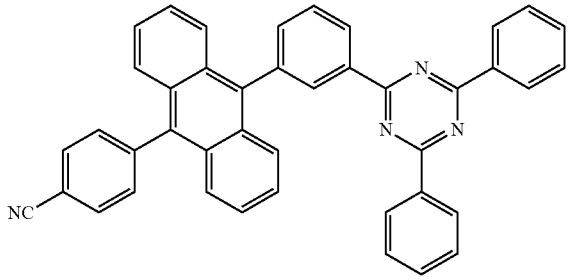

(D)

-continued

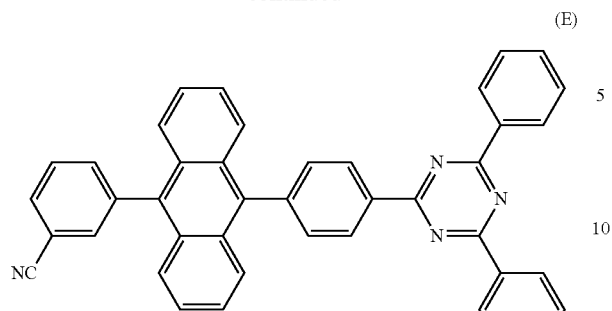
(E)

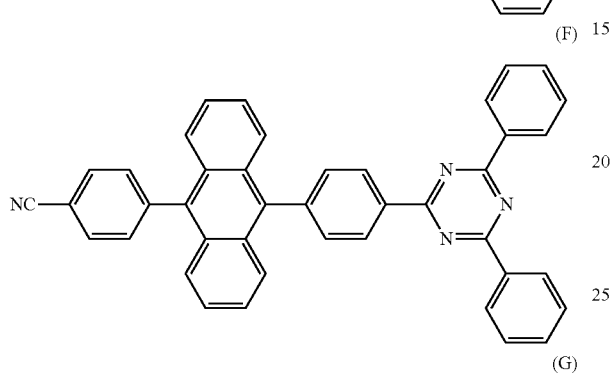
(F)

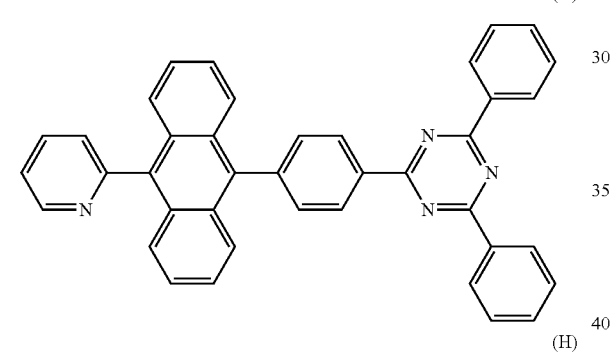
(G)

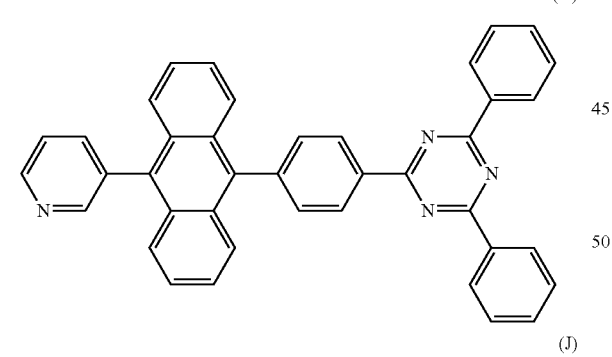
(H)

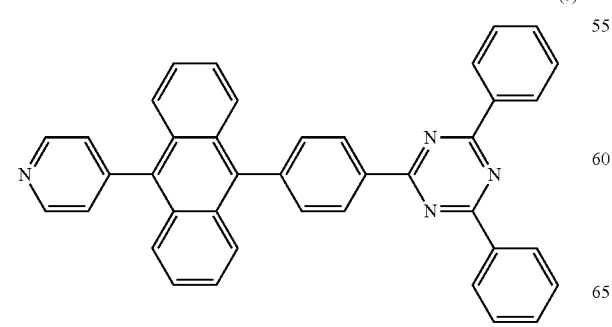
(J)

-continued

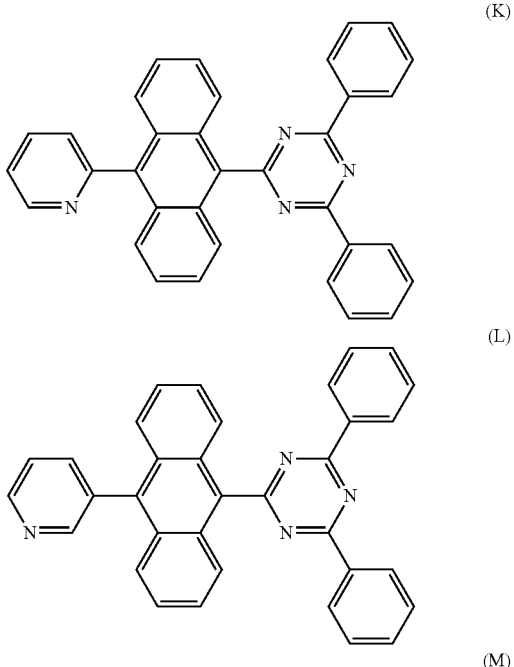
(K)

(L)

(M)

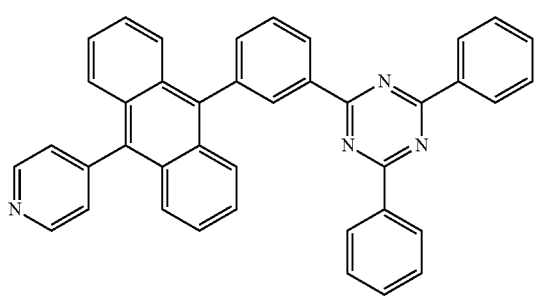

Particularly good performance characteristics are obtained when the compound of formula 1 is chosen from this selection.

The object is further achieved by an organic semiconducting layer comprising the inventive compound.

According to an aspect of the invention the organic semiconducting layer may be used for an organic electronic device. For example the organic electronic device can be an OLED or there like.

The compounds represented by formula 1 have strong electron transport characteristics to increase charge mobility and/or stability and thereby to improve luminance efficiency, voltage characteristics, and/or life-span characteristics.

The compounds represented by formula 1 have high electron mobility and a low operating voltage.

According to another aspect of the invention there is provided an organic optoelectronic device comprising an anode layer and a cathode layer facing each other and at least one organic semiconducting layer between the anode layer and the cathode layer, wherein the organic semiconducting layer comprises or consist of the compound of formula I.

According to yet another aspect of the invention there is provided a display device comprising the organic electronic device, which can be an organic optoelectronic device.

The compound according to formula I may comprise at least 7 to 20 aromatic rings, alternatively at least 7 to 15 aromatic rings, alternatively at least 7 to 12 aromatic rings;

and/or the compound of formula I comprises at least 1 to 5, alternatively 2 to 4 or 2 to 3, hetero aromatic rings The compound of formula I may have a dipole moment of about ≥0 and about ≤6 Debye, alternatively about ≥1.5 and about ≥6 Debye.

Surprisingly, it has been found that particularly high conductivity and low operating voltage of an organic semiconducting layer comprising compounds of formula I may be obtained when the dipole moment of compound for formula I is selected in this range.

The reduction potential (or LUMO) of the compound of formula I may be selected more negative than −1.9 V and less negative than −2.6 V against Fc/Fc$^+$ in tetrahydrofuran, alternatively more negative than −2V and less negative than −2.5 V.

The compound of formula I may have a glass transition temperature Tg of about ≥100° C. and About ≤380° C., alternatively about ≥110° C. and about ≤350° C., alternatively about ≥150° C. and about ≤320° C.

The compound of formula I may have a glass transition temperature Tg of about ≥110° C. and about ≤150° C.

The compound of formula I may have a rate onset temperature $T_{RO}$ of about ≥220° C. and ≤400° C., alternatively about ≥230° C. and about ≤380° C.

The organic semiconducting layer may further comprise an additive, selected from the group consisting of metal, metal salt or organic alkali metal complex. The additive may be alkali metal additive. The additive may be an alkali metal complex or an alkali metal salt. The additive may be 8-hydroxyquinolinolato lithium, an alkali borate or an alkali phenolate. The additive may be 8-hydroxyquinolinatolithium or lithium tetra(1H-pyrazol-1-yl)borate. Combination of the inventive compounds with the respective additives is particular helpful for improving the performance of the respective organic semiconducting layer.

The additive may be comprised in the organic semiconducting layer in an amount from 1 to 99 vol % with respect to the total volume of the organic semiconducting layer. The concentration of the additive may be from 10 to 90 vol %, alternatively from 20 to 80 vol %, alternatively from 30 to 70 vol %, alternatively from 30 to 50 vol %.

The object is further achieved by an organic electronic device comprising, between an anode and a cathode and an electrical contact with the anode and the cathode, the inventive organic semiconducting layer.

The organic electronic device may further comprise an emission layer, wherein the organic semiconductive layer is arranged between the emission layer and the cathode. When used in such a layer, the advantages coming along with the use of the inventive compounds were particularly pronounced.

Finally, the object is achieved by a device which is a display device or a lighting device, the device comprising the inventive organic electronic device.

It was surprising found that the inventive compounds may advantageously be used as an electron transporting host in organic light emitting diodes (OLEDs), in particular in combination with suitable additives, such as alkali organic salts or alkali organic complexes. It was further surprisingly found that the use of the inventive compounds results in improved device performance, in particular with respect to d/A efficiency.

Surprisingly, it was found that the compounds of formula 1 and the inventive organic electronic devices solve the problem underlying the present invention by being superior over the organic electroluminescent devices and compounds known in the art, in particular with respect to cd/A efficiency, also referred to as current efficiency. At the same time the operating voltage is kept at a similar or even improved level which is important for reducing power consumption and increasing battery life, for example of a mobile display device. High cd/A efficiency is important for high efficiency and thereby increased battery life of a mobile device, for example a mobile display device.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of cd/A efficiency. These compounds are discussed herein to be particularly preferred.

Further an organic optoelectronic device having high efficiency and/or long life-span may be realized.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either the first electrode or the second electrode may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide (SnO2), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

The hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 1 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate (PANI/PSS).

The HIL may be a pure layer of p-type dopant and the p-type dopant may be selected from tetrafluoro-tetracyano-quinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyano-quinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. α-NPD doped with 2,2',2"-(cyclopropane-1,2,3-triylidene)tris(2-(p-cyanotetrafluorophenyl)acetonitrile). Dopant concentrations can be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

The hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of the electron blocking layer (EBL) is to prevent electrons from being transferred from the emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

The electron blocking layer may comprise a compound of formula Z below (Z).

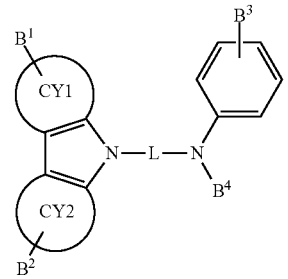

In Formula Z, CY1 and CY2 are the same as or different from each other, and each independently represent a benzene cycle or a naphthalene cycle, $B^1$ to $B^3$ are the same as or different from each other, and each independently selected from the group consisting of hydrogen; a substituted or unsubstituted aryl group having 6 to 30 carbon atoms; and a substituted or unsubstituted heteroaryl group having 5 to 30 carbon atoms, $B^4$ is selected from the group consisting of a substituted or unsubstituted phenyl group, a substituted or unsubstituted biphenyl group, a substituted or unsubstituted terphenyl group, a substituted or unsubstituted triphenylene group, and a substituted or unsubstituted heteroaryl group having 5 to 30 carbon atoms, L is a substituted or unsubstituted arylene group having 6 to 30 carbon atoms.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML) The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBI), 3-tert-butyl-9,10-di-2-naphthylanthracenee (TBADN), distyrylarylene (DSA), bis(2-(2-hydroxyphenyl)benzo-thiazolate)zinc (Zn(BTZ)2), G3 below, "AND", Compound 1 below, and Compound 2 below.

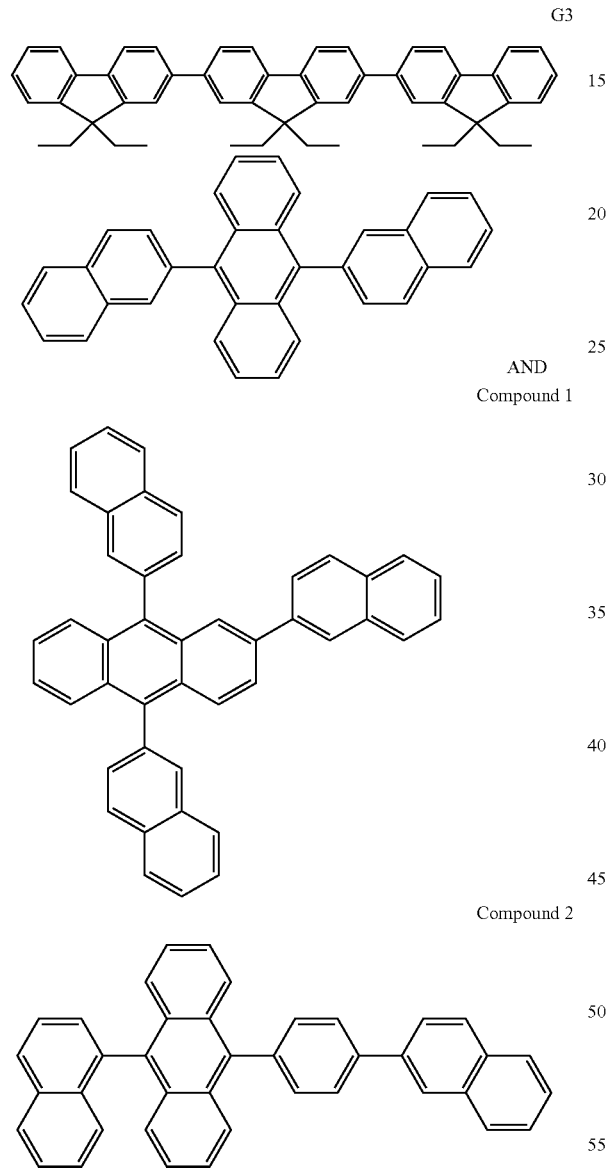

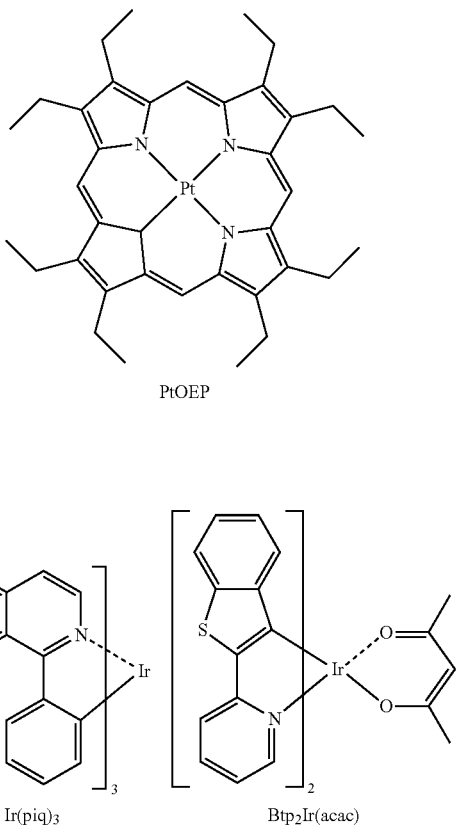

PtOEP

Ir(piq)3    Btp2Ir(acac)

Examples of phosphorescent green emitter dopants are Ir(ppy)3 (ppy=phenylpyridine), Ir(ppy)2(acac), Ir(mpyp)3 are shown below. Compound 3 is an example of a fluorescent green emitter and the structure is shown below.

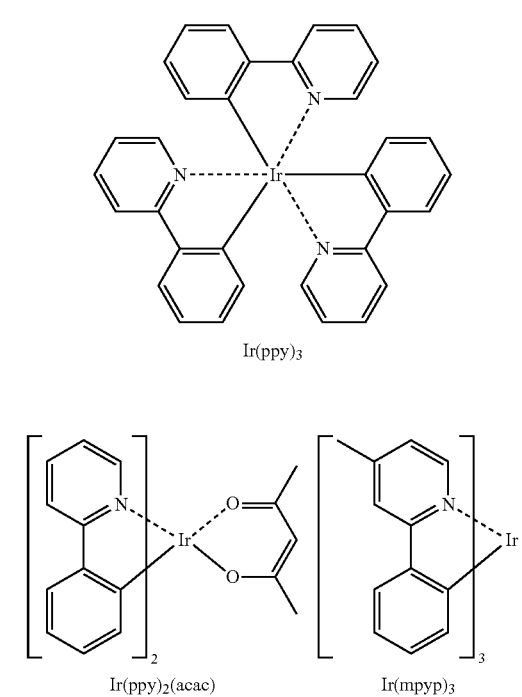

Ir(ppy)3

Ir(ppy)2(acac)    Ir(mpyp)3

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

-continued

Compound 3

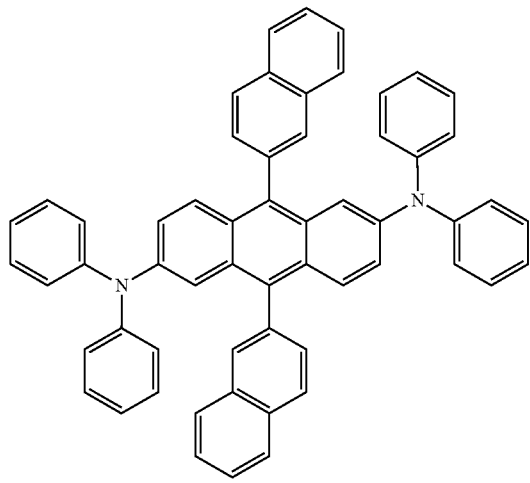

Examples of phosphorescent blue emitter dopants are F2Irpic, (F2ppy)2Ir(tmd) and Ir(dfppz)3, ter-fluorene, the structures are shown below. 4.4'-bis(4-diphenyl amiostyryl) biphenyl (DPAVBi), 2,5,8,11-tetra-tert-butyl perylene (TBPe), and Compound 4 below are examples of fluorescent blue emitter dopants

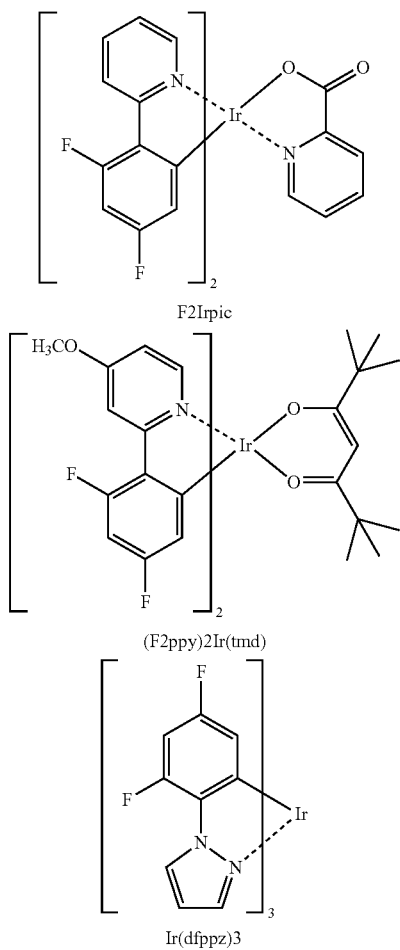

F2Irpic (F2ppy)2Ir(tmd)

Ir(dfppz)3

-continued

Compound 4

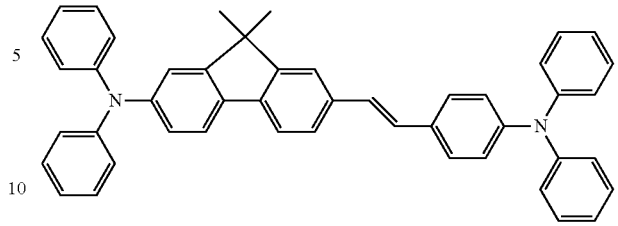

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may contain an electron transport layer (ETL). In accordance with the invention, the electron transport layer may be the inventive organic semiconducting layer comprising the inventive compound represented by the general formula (I) as defined above.

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general formula (I) as defined above as the organic electron transport matrix (ETM) material. The electron transport layer may comprise, besides the compound represented by the general formula (I), further ETM materials known in the art. Likewise, the electron transport layer may comprise as the only electron transport matrix material the compound represented by general formula (I). In case that the inventive organic electronic device comprises more than one electron transport layers, the compound represented by the general formula (I) may be comprised in only one of the electron transport layers, in more than one of the electron transport layers or in all of the electron transport layers. In accordance with the invention, the electron transport layer may comprise, besides the ETM material, at least one additive as defined below. Further, the electron transport layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1970 371 A1 or WO 2013/079217A1.

Electron Injection Layer (EIL)

The optional EIL, which may facilitates injection of electrons from the cathode, may be formed on the ETL, preferably directly on the electron transport layer. Examples of materials for forming the EIL include lithium 8-hydroxy-quinolinolate (LiQ), LiF, NaCl, CsF, Li$_2$O, BaO, Ca, Ba, Yb, Mg which are known in the art. Deposition and coating conditions for forming the EIL are similar to those for formation of the HIL, although the deposition and coating conditions may vary, according to the material that is used to form the EIL.

The thickness of the EIL may be in the range from about 0.1 nm to about to nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxides, such as ITO or IZO.

The thickness of the cathode electrode may be in the range from about 5 nm to about 1000 nm, for example, in the range from about to nm to about too nm. When the thickness of the cathode electrode is in the range from about 5 nm to about 50 nm, the cathode electrode may be transparent or semi-transparent even if formed from a metal or metal alloy.

It is to be understood that the cathode electrode is not part of an electron injection layer or the electron transport layer.

Charge Generation Layer/Hole Generating Layer

The charge generation layer (CGL) may be composed of a double layer.

Typically, the charge generation layer is a pn junction joining a n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, FeF3, and SbCl5. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4'-diamine (TPD) and N,N',N'-tetranaphthyl-benzidine (TNB).

The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline) aluminum, benzazole derivatives, and silole derivatives.

In one embodiment, the n-type charge generation layer may include compounds of the following Chemical Formula X.

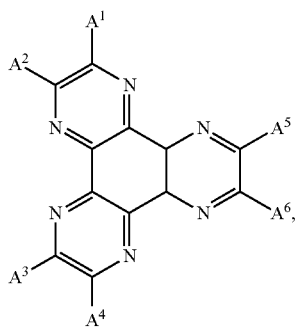 (X)

wherein each of $A^1$ to $A^6$ may be hydrogen, a halogen atom, nitrile (—CN), nitro (—NO2), sulfonyl (—SO2R), sulfoxide (—SOR), sulfonamide (—SO2NR), sulfonate (—SO3R), trifluoromethyl (—CF3), ester (—COOR), amide (—CONHR or —CONRR'), substituted or unsubstituted straight-chain or branched-chain C1-C12 alkoxy, substituted or unsubstituted straight-chain or branched-chain C1-C12 alkyl, substituted or unsubstituted straight-chain or branched chain C2-C12 alkenyl, a substituted or unsubstituted aromatic or non-aromatic heteroring, substituted or unsubstituted aryl, substituted or unsubstituted mono- or di-arylamine, substituted or unsubstituted aralkylamine, or the like. Herein, each of the above R and R' may be substituted or unsubstituted C1-C60 alkyl, substituted or unsubstituted aryl, or a substituted or unsubstituted 5- to 7-membered heteroring, or the like.

An example of such n-type charge generation layer may be a layer comprising CNHAT

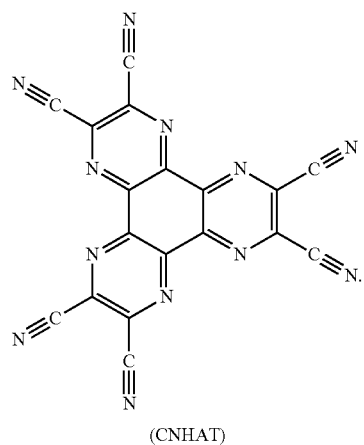

(CNHAT)

The hole generating layer is arranged on top of the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an electron transport layer, and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an electron transport layer, an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacent arranged to an anode electrode, the anode electrode is adjacent arranged to a first hole injection layer, the first hole injection layer is adjacent arranged to a first hole transport layer, the first hole transport layer is adjacent arranged to a first electron blocking layer, the first electron blocking layer is adjacent arranged to a first emission layer, the first emission layer is adjacent arranged to a first electron transport layer, the first electron transport layer is adjacent arranged to an n-type charge generation layer, the n-type charge generation layer is adjacent arranged to a hole generating layer, the hole generating layer is adjacent arranged to a second hole transport layer, the second hole transport layer is adjacent arranged to a second electron blocking layer, the second electron blocking layer is adjacent arranged to a second emission layer, between the second emission layer and the cathode electrode an optional electron transport layer and/or an optional injection layer are arranged.

For example, the OLED according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound according to formula I.

An organic electronic device according to one embodiment may include a substrate, an anode layer, an organic semiconducting layer comprising a compound of formula 1 and a cathode layer. An organic electronic device according to one embodiment comprises at least one organic semiconducting layer comprising at least one compound of formula I, at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of formula 1, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:
- at least one deposition source, preferably two deposition sources and more preferred at least three deposition sources.

The methods for deposition that can be suitable comprise:
deposition via vacuum thermal evaporation;
deposition via solution processing, preferably the processing is selected from spin-coating, printing, casting; and/or
slot-die coating.

According to various embodiments of the present invention, there is provided a method using:
- a first deposition source to release the compound of formula 1 according to the invention, and
- a second deposition source to release the alkali halide or alkali organic complex, preferably a lithium halide or lithium organic complex;

the method comprising the steps of forming the electron transport layer stack; whereby for an organic light-emitting diode (OLED):
- the first electron transport layer is formed by releasing the compound of formula 1 according to the invention from the first deposition source and an alkali metal compound, preferably an alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
- on a substrate a first anode electrode is formed,
- on the first anode electrode an emission layer is formed,
- on the emission layer an electron transport layer stack is formed, preferably a first electron transport layer is formed on the emission layer and optional a second electron transport layer is formed,
- and finally a cathode electrode is formed,
- optional a hole injection layer, a hole transport layer, and a hole blocking layer, formed in that order between the first anode electrode and the emission layer,
- optional an electron injection layer is formed between the electron transport layer and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:
anode, hole injection layer, first hole transport layer, second hole transport layer, emission layer, optional second electron transport layer, first electron transport layer comprising a compound of formula 1 according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples. Reference will now be made in detail to the exemplary aspects.

DETAILS AND DEFINITIONS OF THE INVENTION

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and isopropyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed shall be any further aromatic hydrocarbon substituents, such as fluorenyl etc. Arylene, respectively heteroarylene refers to groups to which two further moieties are attached. In the present specification "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The arylene group may include a monocyclic, polycyclic or fused ring polycyclic (i.e., rings sharing adjacent pairs of carbon atoms) functional group.

The term "heteroaryl" or "hereroarylene" as used herein refers to aryl groups in which at least one carbon atom is substituted by a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation.

The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroarylene" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED). A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural formula.

The energy levels of the highest occupied molecular orbital, also named HOMO, and of the lowest unoccupied molecular orbital, also named LUMO, are measured in electron volt (eV) indirectly by cyclic voltammetry vs ferrocene or can be calculated using simulation B3LYP with a 6-31G* basis set.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emitting" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound of formula I is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milli-Ampere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

The term "life-span" and "lifetime" are simultaneously used and have the same meaning.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities. It should be noted that, as used in this specification and the appended claims, the singular forms "a", "an", and "the" include plural referents unless the content clearly dictates otherwise.

The anode electrode and cathode electrode may be described as anode electrode/cathode electrode or anode electrode/cathode electrode or anode electrode layer/cathode electrode layer.

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom in the molecule.

The dipole moment is determined by a semi-empirical molecular orbital method.

The partial charges and atomic positions in the gas phase are obtained using the hybrid functional B3LYP with a 6-31G* basis set as implemented in the program package TURBOMOLE V6.5. If more than one conformation is viable, the conformation with the lowest total energy is selected to determine the dipole moment.

The reduction potential may be determined by cyclic voltammetry with potentiostatic device Metrohm PGSTAT30 and software Metrohm Autolab GPES at room temperature. The redox potentials are measured in an argon de-aerated, anhydrous 0.1M THF solution of the compound of formula I, under argon atmosphere, with 0.1M tetrabutylammonium hexafluorophosphate as supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run is done in the broadest range of the potential set on the working electrodes, and the range is then adjusted within subsequent runs appropriately. The final three runs are done with the addition of ferrocene (in 0.1M concentration) as the standard. The average of potentials corresponding to cathodic and anodic peak of the compound is determined through subtraction of the average of cathodic and anodic potentials observed for the standard $Fc^+/F$ redox couple.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
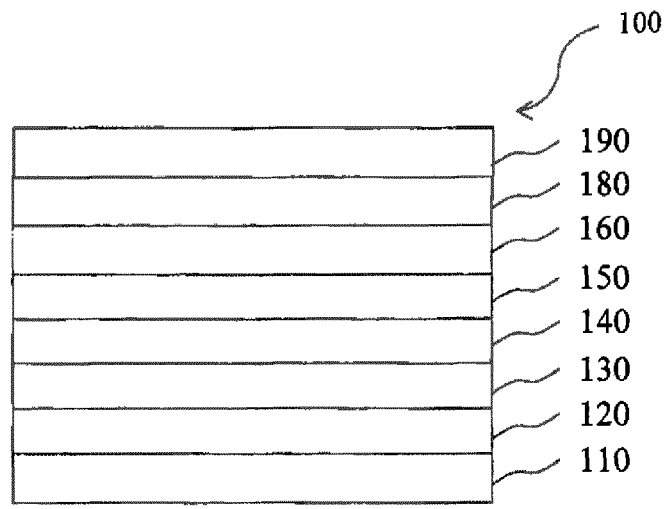
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
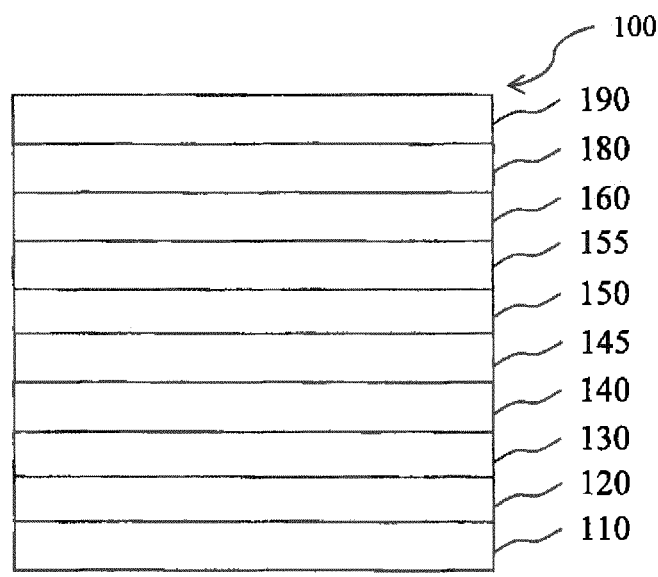
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Figure 3:
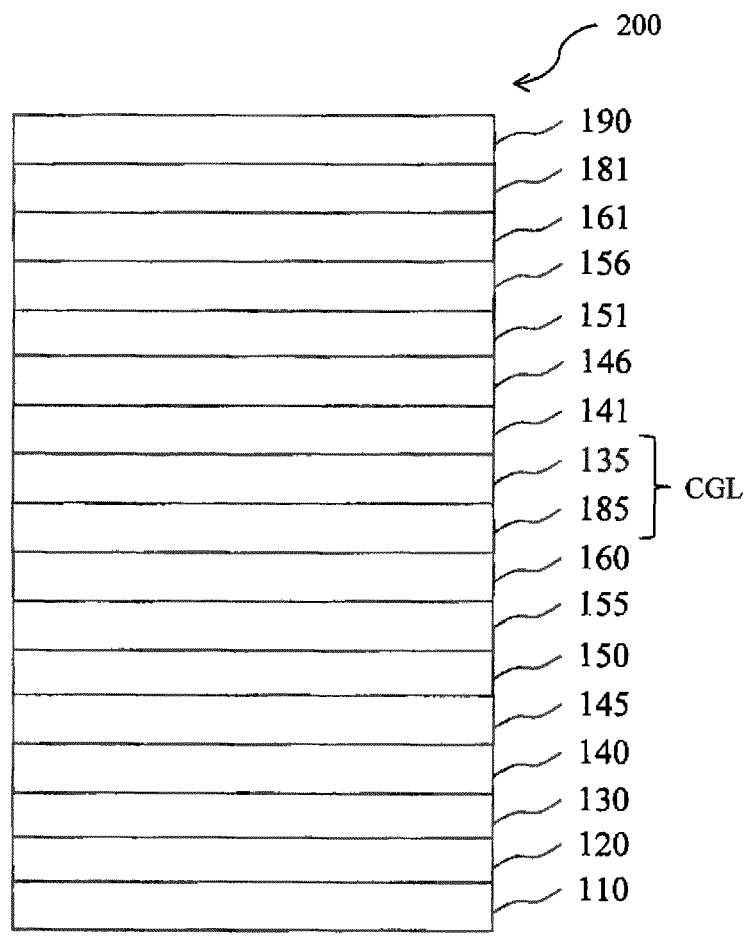
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate no, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Preparation of the Inventive Compounds

Synthesis

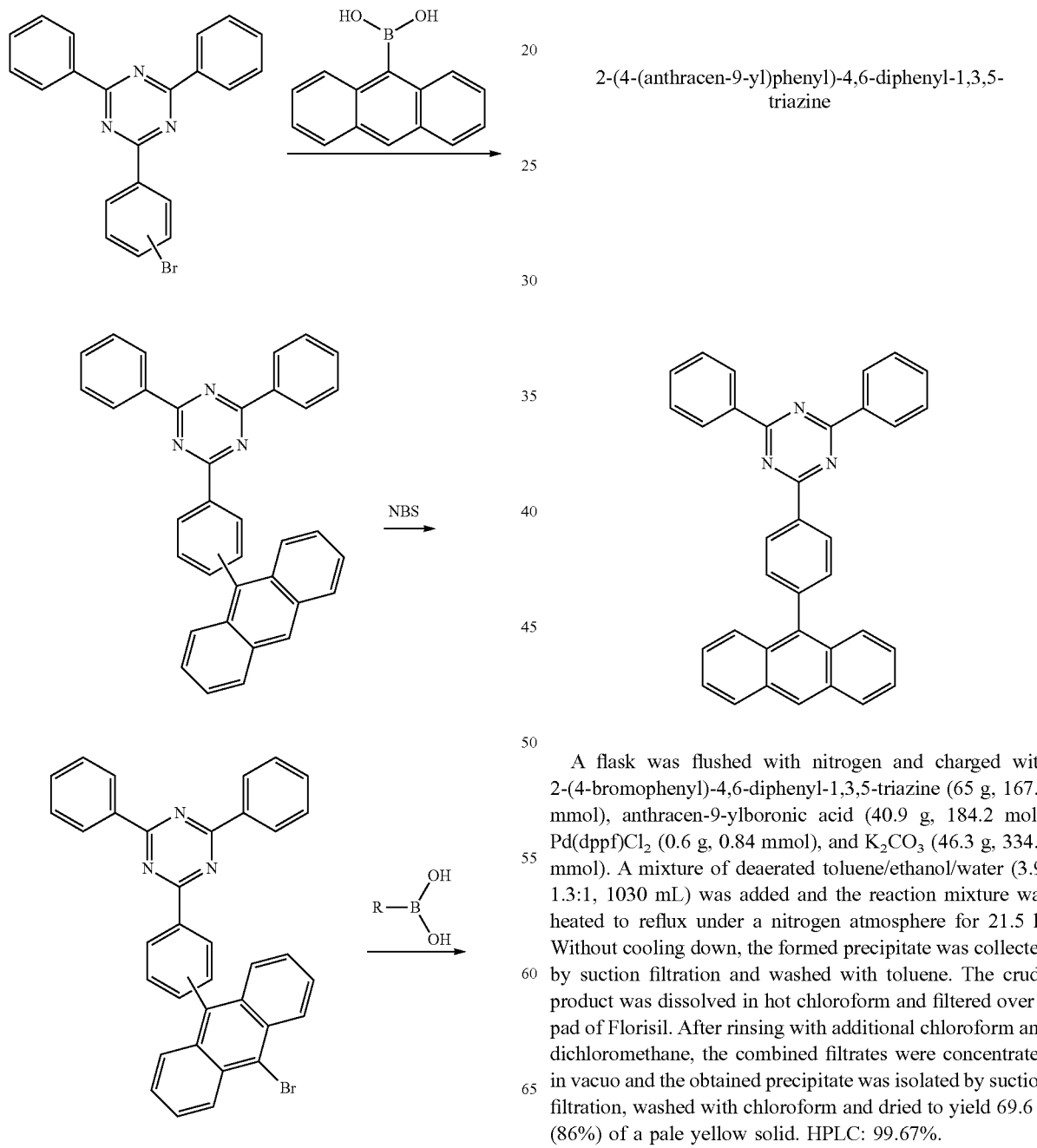

2-(4-(anthracen-9-yl)phenyl)-4,6-diphenyl-1,3,5-triazine

A flask was flushed with nitrogen and charged with 2-(4-bromophenyl)-4,6-diphenyl-1,3,5-triazine (65 g, 167.4 mmol), anthracen-9-ylboronic acid (40.9 g, 184.2 mol), Pd(dppf)Cl$_2$ (0.6 g, 0.84 mmol), and K$_2$CO$_3$ (46.3 g, 334.8 mmol). A mixture of deaerated toluene/ethanol/water (3.9:1.3:1, 1030 mL) was added and the reaction mixture was heated to reflux under a nitrogen atmosphere for 21.5 h. Without cooling down, the formed precipitate was collected by suction filtration and washed with toluene. The crude product was dissolved in hot chloroform and filtered over a pad of Florisil. After rinsing with additional chloroform and dichloromethane, the combined filtrates were concentrated in vacuo and the obtained precipitate was isolated by suction filtration, washed with chloroform and dried to yield 69.6 g (86%) of a pale yellow solid. HPLC: 99.67%.

2-(4-(10-bromoanthracen-9-yl)phenyl)-4,6-diphenyl-1,3,5-triazine

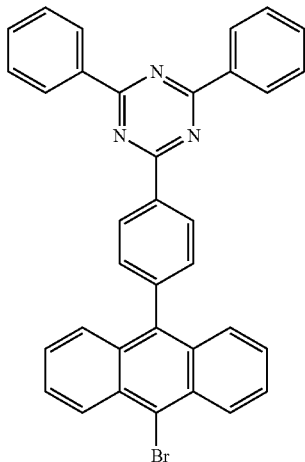 [SMILES: Brc1c2ccccc2c(-c2ccc(-c3nc(-c4ccccc4)nc(-c4ccccc4)n3)cc2)c2ccccc12]

A flask was charged with 2-(4-(10-bromoanthracen-9-yl)phenyl)-4,6-diphenyl-1,3,5-triazine (40 g, 82.4 mmol), N-bromosuccinimide (16.1 g, 90.6 mmol) and chloroform (1120 mL). The mixture was refluxed in total for 92 h. After 47 and after 70 h, additional N-bromosuccinimide was added (14.7 g, 82.6 mmol each). After cooling down to room temperature, the reaction mixture was extracted with water three times. The organic phase was dried over MgSO$_4$, filtered and evaporated to dryness. After repeated recrystallization from toluene and drying, 33.5 g (72%) of a yellow solid were obtained. HPLC: 99.88%.

2-(3-(anthracen-9-yl)phenyl)-4,6-diphenyl-1,3,5-triazine

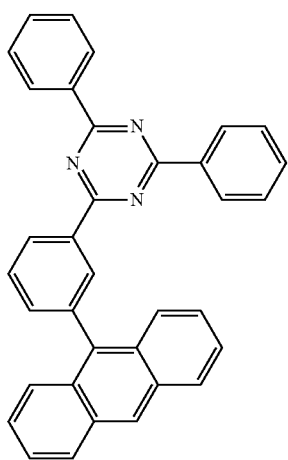 [SMILES: c1ccc(-c2nc(-c3ccccc3)nc(-c3cccc(-c4c5ccccc5cc5ccccc45)c3)n2)cc1]

A flask was flushed with nitrogen and charged with 2-(3-bromophenyl)-4,6-diphenyl-1,3,5-triazine (50 g, 128.8 mmol), anthracen-9-ylboronic acid (31.5 g, 141.7 mol), Pd(dppf)Cl$_2$ (0.47 g, 0.64 mmol), and K$_2$CO$_3$ (35.6 g, 257.6 mmol). A mixture of deaerated toluene/ethanol/water (3.9:13:1, 800 mL) was added and the reaction mixture was heated to reflux under a nitrogen atmosphere for 22 h. After cooling down to room temperature, the formed precipitate was collected by suction filtration and washed with toluene, methanol, water (until pH-neutral) and methanol. After drying, 56.4 g (90%) of a white solid were obtained. HPLC: 99.91%.

2-(3-(10-bromoanthracen-9-yl)phenyl)-4,6-diphenyl-1,3,5-triazine

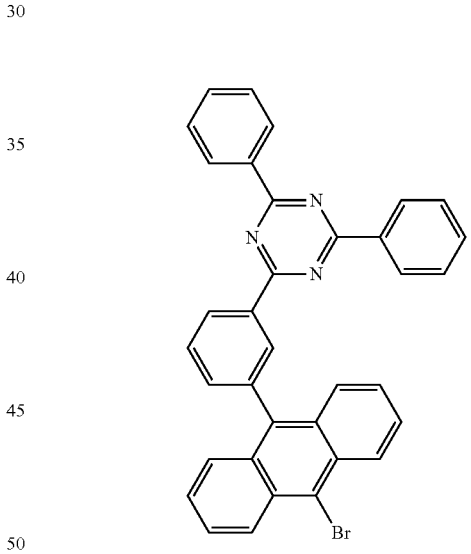

A flask was charged with 2-(3-(anthracen-9-yl)phenyl)-4,6-diphenyl-1,3,5-triazine (31.3 g, 64.5 mmol), N-bromosuccinimide (12.6 g, 70.8 mmol) and chloroform (640 mL). The mixture was refluxed in total for 26 h. After 4 h and after 22 h, additional N-bromosuccinimide was added (3.4 g, 19.3 mmol and 1.7 g, 9.6 mmol, respectively). After cooling down to room temperature, the reaction mixture was extracted with water three times. The organic phase was dried over MgSO$_4$ and filtered. The filtrate was concentrated in vacuo and n-hexane was added. The resulting precipitate was collected by suction filtration, washed with n-hexane and dried to afford 33.1 g (91%) of a pale yellow solid. HPLC: 98.97%.

3-(10-(4-(4,6-diphenyl-1,3,5-triazin-2-yl)phenyl)anthracen-9-yl)benzonitrile

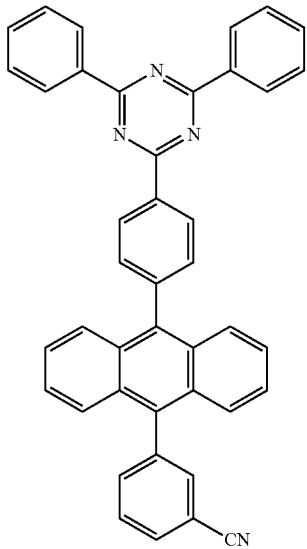 [SMILES: N#Cc1cccc(-c2c3ccccc3c(-c3ccc(-c4nc(-c5ccccc5)nc(-c5ccccc5)n4)cc3)c3ccccc23)c1]

A flask was flushed with nitrogen and charged with 2-(4-(10-bromoanthracen-9-yl)phenyl)-4,6-diphenyl-1,3,5-triazine (10 g, 17.7 mmol), 3-cyanophenylboronic acid (3.38 g, 23.0 mmol), Pd(dppf)Cl$_2$ (0.26 g, 0.35 mmol), and K$_2$CO$_3$ (4.9 g, 35.4 mmol). A mixture of deaerated THF/water (6.6:1, 230 mL) was added and the reaction mixture was heated to reflux under a nitrogen atmosphere for 17 h. After cooling down to room temperature, the formed precipitate was collected by suction filtration and washed with n-hexane. The solid was dissolved in dichloromethane and the organic phase was extracted with water three times, dried over MgSO$_4$, filtered and concentrated in vacuo. After addition of n-hexane, the formed precipitate was collected by suction filtration and washed with n-hexane. After recrystallization from chlorobenzene and drying, 6.1 g (60%) of a pale yellow solid were obtained. Final purification was achieved by sublimation. HPLC/ESI-MS: 100%, m/z=587 ([M+H]$^+$).

4-(10-(3-(4,6-diphenyl-1,3,5-triazin-2-yl)phenyl)anthracen-9-yl)benzonitrile

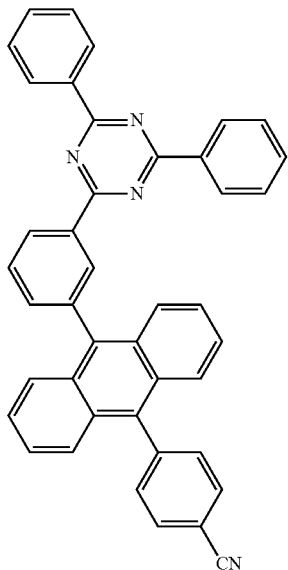 [SMILES: N#Cc1ccc(-c2c3ccccc3c(-c3cccc(-c4nc(-c5ccccc5)nc(-c5ccccc5)n4)c3)c3ccccc23)cc1]

A flask was flushed with nitrogen and charged with 2-(3-(10-bromoanthracen-9-yl)phenyl)-4,6-diphenyl-1,3,5-triazine (10 g, 17.7 mmol), 4-cyanophenylboronic acid (3.38 g, 23.0 mmol), Pd(PPh$_3$)$_4$ (0.61 g, 0.53 mmol), and K$_2$CO$_3$ (7.3 g, 53.1 mmol). A mixture of deaerated 1,4-dioxane/water (2.6:1, 100 mL) was added and the reaction mixture was heated to 90° C. under a nitrogen atmosphere for 20.5 h. After cooling down to room temperature, the formed precipitate was collected by suction filtration and washed with 1,4-dioxane, water (until pH neutral) and methanol. After drying, the crude product was purified by silica gel filtration. The impurities were rinsed with n-hexane and, subsequently, the product was rinsed with hot chloroform. The product-containing filtrate was concentrated, toluene was added, and the resulting mixture was further concentrated until precipitation begins. After stirring for 1 h at room temperature, the precipitate was collected by suction filtration and washed with toluene and n-hexane. After drying, 4.81 g (46%) of a pale yellow solid were obtained. Final purification was achieved by sublimation. HPLC/ESI-MS: 100%, m/z=587 ([M+H]$^+$).

3-(10-(3-(4,6-diphenyl-1,3,5-triazin-2-yl)phenyl)anthracen-9-yl)benzonitrile

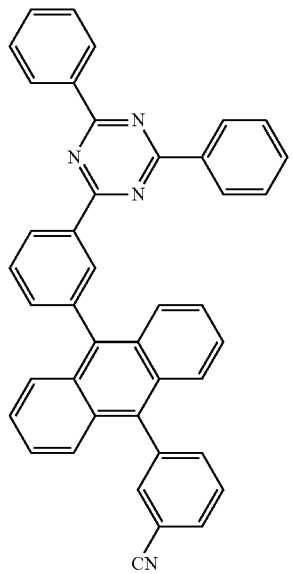 [SMILES: N#Cc1cccc(-c2c3ccccc3c(-c3cccc(-c4nc(-c5ccccc5)nc(-c5ccccc5)n4)c3)c3ccccc23)c1]

A flask was flushed with nitrogen and charged with 2-(3-(10-bromoanthracen-9-yl)phenyl)-4,6-diphenyl-1,3,5-triazine (4.8 g, 8.5 mmol), 3-cyanophenylboronic acid (1.62 g, 11.1 mmol), Pd(PPh$_3$)$_4$ (0.3 g, 0.26 mmol), and K$_2$CO$_3$ (3.53 g, 26.5 mmol). A mixture of deaerated 1,4-dioxane/water (4.2:1, 70 mL) was added and the reaction mixture was heated to 90° C. under a nitrogen atmosphere for 38 h. After cooling down to room temperature, the formed precipitate was collected by suction filtration and washed with 1,4-dioxane, n-hexane, water (until pH neutral) and n-hexane. The solid was dissolved in hot chloroform and filtered over a pad of Florisil. After rinsing with additional hot chloroform, the filtrates were combined, n-heptane was added and the chloroform was removed in vacuo. The resulting suspension was filtered and the obtained solid was washed with n-heptane, acetonitrile and methanol. Subsequently, the solid was dissolved in hot toluene, filtered over a pad of Florisil and the filtrate was evaporated to dryness. The remaining solid was dissolved in dichloromethane and precipitation was induced by addition of n-hexane. The obtained solid was isolated by suction filtration and washed with n-hexane. After drying, 3.67 g (77%) of a white solid were obtained. Final purification was achieved by sublimation. HPLC/ESI-MS: 100%, m/z=587 ([M+H]$^+$), 609 ([M+Na]$^+$).

2,4-diphenyl-6-(3-(10-(pyridin-4-yl)anthracen-9-yl)phenyl)-1,3,5-triazine

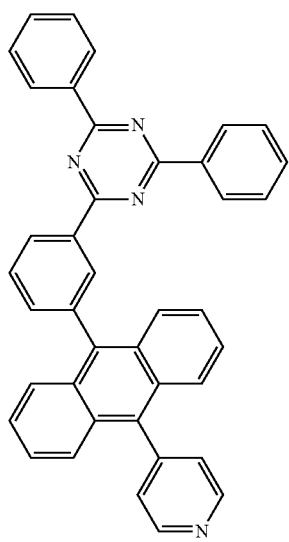 [SMILES: c1ccc(-c2nc(-c3ccccc3)nc(-c3cccc(-c4c5ccccc5c(-c5ccncc5)c5ccccc45)c3)n2)cc1]

A flask was flushed with nitrogen and charged with 2-(3-(10-bromoanthracen-9-yl)phenyl)-4,6-diphenyl-1,3,5-triazine (10.0 g, 17.7 mmol), pyridin-4-ylboronic acid (2.8 g, 23.0 mol), K$_2$CO$_3$ (7.3 g, 53.1 mmol), and Pd(PPh$_3$)$_4$ (0.61 g, 0.5 mmol). A mixture of deaerated 1,4-dioxane/water (5:1, 162 mL) was subsequently added and the reaction mixture was heated to 100° C. under a nitrogen atmosphere for 4 days. After cooling down to room temperature, the resulting precipitate was isolated by suction filtration and washed with water. Further purification was achieved by column chromatography (silica, toluene then chloroform/ethyl acetate 10:1) followed by recrystallization from methanol to yield 2.8 g (66%) of a beige solid after drying. Final purification was achieved by sublimation. HPLC/ESI-MS: 100%, m/z=563 ([M+H]$^+$).

2,4-diphenyl-6-(3-(10-(pyridin-3-yl)anthracen-9-yl)phenyl)-1,3,5-triazine

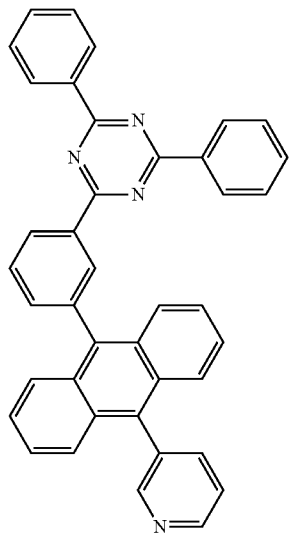 [SMILES: c1ccc(-c2nc(-c3ccccc3)nc(-c3cccc(-c4c5ccccc5c(-c5cccnc5)c5ccccc45)c3)n2)cc1]

A flask was flushed with nitrogen and charged with 2-(3-(1-bromoanthracen-9-yl)phenyl)-4,6-diphenyl-1,3,5-triazine (4.8 g, 8.5 mmol), 3-(4,4,5,5-tetramethyl-1,3,2-dioxaborolan-2-yl)pyridine (2.26 g, 11.05 mmol), Pd(PPh$_3$)$_4$ (0.29 g, 0.25 mmol), and K$_2$CO$_3$ (3.52 g, 25.5 mmol). A mixture of deaerated 1,4-dioxane/water (3:1, 52 mL) was added and the reaction mixture was heated to 90° C. under a nitrogen atmosphere for 12 h. After cooling down to 35° C., the resulting precipitate was isolated by suction filtration and washed with water. The obtained light-grey solid was dissolved in chloroform and the organic phase was filtered over a pad of Florisil. After rinsing with additional chloroform, the colorless filtrate was evaporated to dryness, and the residue recrystallized from chlorobenzene. The resulting white precipitate was isolated by suction filtration and washed with n-heptane, acetonitrile, and acetonitrile/methanol 1:1. Further purification was achieved by recrystallization from toluene/hexane to yield 2.6 g (54%) of a yellow solid after drying. Final purification was achieved by sublimation. HPLC/ESI-MS: 100%, m/z=563 ([M+H]$^+$).

2,4-diphenyl-6-(4-(10-(pyridin-3-yl)anthracen-9-yl)phenyl)-1,3,5-triazine

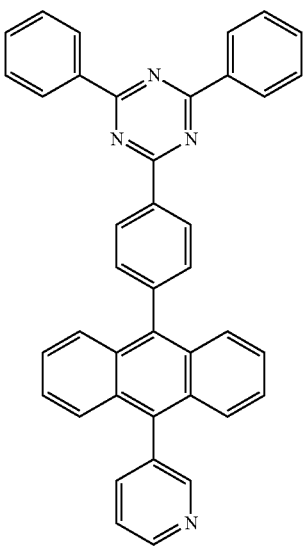 [SMILES: c1ccc(-c2nc(-c3ccccc3)nc(-c3ccc(-c4c5ccccc5c(-c5cccnc5)c5ccccc45)cc3)n2)cc1]

A flask was flushed with nitrogen and charged with 2-(4-(10-bromoanthracen-9-yl)phenyl)-4,6-diphenyl-1,3,5-triazine (10.0 g, 17.7 mmol), 3-(4,4,5,5-tetramethyl-1,3,2-dioxaborolan-2-yl)pyridine (15.4 g, 75.0 mmol), Pd(dppf)Cl$_2$ (0.52 g, 0.7 mmol), tetrabutylammonium bromide (0.6 g, 1.7 mmol), and K$_2$CO$_3$ (19.6 g, 141.8 mmol). A mixture of deaerated THF/water (4:1, 360 mL) was added and the reaction mixture was heated to 75° C. under a nitrogen atmosphere for 5 days. After cooling down to 5° C., the resulting precipitate was isolated by suction filtration and washed with THF. The crude product was purified by column chromatography (silica, dichloromethane/hexane 1:1 to dichloromethane/methanol 99:1). Further purification was achieved by recrystallization from hexane to yield 4.4 g (44%) of a yellow solid after drying. Final purification was achieved by sublimation. HPLC/ESI-MS: 100%, m/z=563 ([M+H]$^+$).

2,4-diphenyl-6-(4-(10-(pyridin-4-yl)anthracen-9-yl)phenyl)-1,3,5-triazine

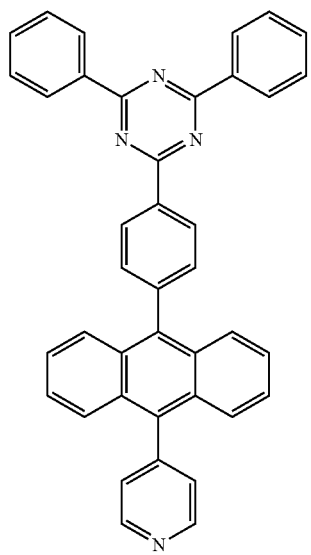 [SMILES: c1ccc(-c2nc(-c3ccccc3)nc(-c3ccc(-c4c5ccccc5c(-c5ccncc5)c5ccccc45)cc3)n2)cc1]

A flask was flushed with nitrogen and charged with 2-(4-(10-bromoanthracen-9-yl)phenyl)-4,6-diphenyl-1,3,5-triazine (10.0 g, 17.7 mmol), pyridin-4-ylboronic acid (8.7 g, 70.8 mmol), Pd(dppf)Cl$_2$ (0.54 g, 0.7 mmol), tetrabutylammonium bromide (1.0 g, 3.1 mmol), and K$_2$CO$_3$ (19.6 g, 141.8 mmol). A mixture of deaerated THF/water (2:1, 360 mL) was added and the reaction mixture was heated to 75° C. under a nitrogen atmosphere for 4 days. After cooling down to 5° C., the resulting precipitate was isolated by suction filtration and washed with THF and water. The crud product was purified by column chromatography (silica, chloroform to hot chlorobenzene/methanol 99:1) and recrystallization from toluene to yield 7.0 g (70%) of a yellow solid after drying. Final purification was achieved by sublimation. HPLC/ESI-MS: 100%, m/z=563 ([M+H]$^+$).

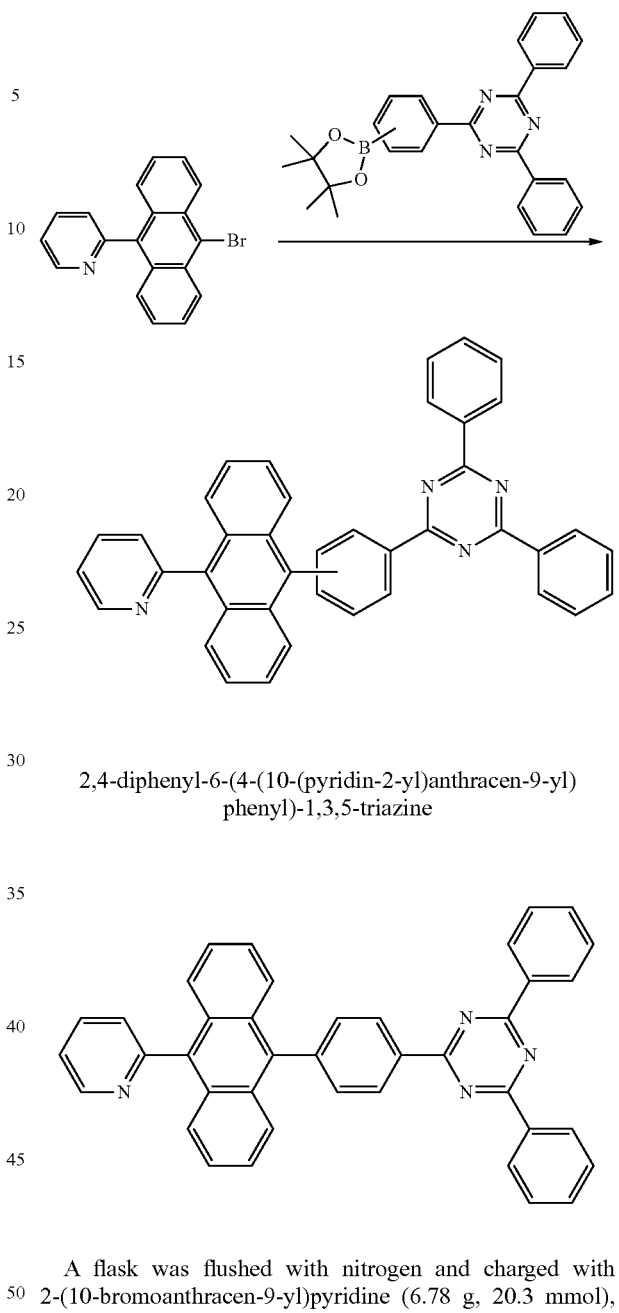

2,4-diphenyl-6-(4-(10-(pyridin-2-yl)anthracen-9-yl)phenyl)-1,3,5-triazine

A flask was flushed with nitrogen and charged with 2-(10-bromoanthracen-9-yl)pyridine (6.78 g, 20.3 mmol), 2,4-diphenyl-6-(4-(4,4,5,5-tetramethyl-1,3,2-dioxaborolan-2-yl)phenyl)-1,3,5-triazine (11.4 g, 26.3 mmol), Pd(PPh$_3$)$_4$ (0.70 g, 0.61 mmol), and K$_2$CO$_3$ (8.41 g, 60.8 mmol). A mixture of deaerated 1,4-dioxane/water (2.6:1, 110 mL) was added and the reaction mixture was heated to 90° C. under a nitrogen atmosphere for 13 h. After cooling down to room temperature, the resulting precipitate was isolated by suction filtration and washed with 1,4-dioxane and water. The solid was dissolved in toluene and extracted with an aq. sodium diethylcarbamodithioate solution and, subsequently, washed with water three times. After drying over MgSO$_4$, the organic phase was concentrated in vacuo. The resulting precipitate was isolated by suction filtration, washed with n-hexane and dried to yield 6.3 g (55%) of a yellow solid. Final purification was achieved by sublimation. HPLC/ESI-MS: 100%, m/z=563 ([M+H]$^+$).

35

2,4-diphenyl-6-(3-(10-(pyridin-2-yl)anthracen-9-yl)phenyl)-1,3,5-triazine

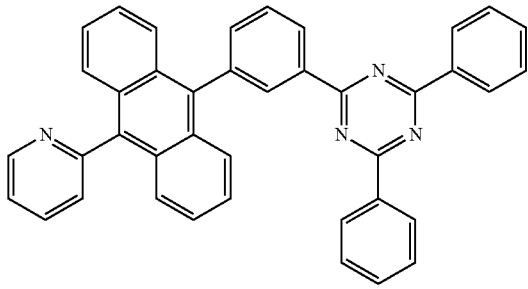 [SMILES: c1ccc(-c2nc(-c3ccccc3)nc(-c3cccc(-c4c5ccccc5c(-c5ccccn5)c5ccccc45)c3)n2)cc1]

A flask was flushed with nitrogen and charged with 2-(10-bromoanthracen-9-yl)pyridine (10.3 g, 31.01 mmol), 2,4-diphenyl-6-(3-(4,4,5,5-tetramethyl-1,3,2-dioxaborolan-2-yl)phenyl)-1,3,5-triazine (15.0 g, 34.45 mmol), Pd(PPh$_3$)$_4$ (1.19 g, 1.0 mmol), and K$_2$CO$_3$ (14.28 g, 103.3 mmol). A mixture of deaerated 1,4-dioxane/water (4:1, 260 mL) was added and the reaction mixture was heated to 90° C. under a nitrogen atmosphere for 31 h. After cooling down to room temperature, the resulting precipitate was isolated by suction filtration and washed with 1,4-dioxane, water, and hexane. The grey solid was dissolved in chloroform and the resulting solution filtered over a pad of Florisil. After rinsing with additional chloroform, the filtrate was concentrated in vacuo to a minimal volume and n-hexane was added. After stirring for 30 min. at 40° C., the mixture was allowed to cool to room temperature and the resulting yellow precipitate was isolated by suction filtration and washed with n-hexane. Further purification was achieved by column chromatography (silica, toluene/chloroform 5:1, and then chloroform/methanol 99:1) to yield 6.0 g (34%) of a yellow solid after drying. Final purification was achieved by sublimation. HPLC/ESI-MS: 100%, m/z=563 ([M+H]$^+$).

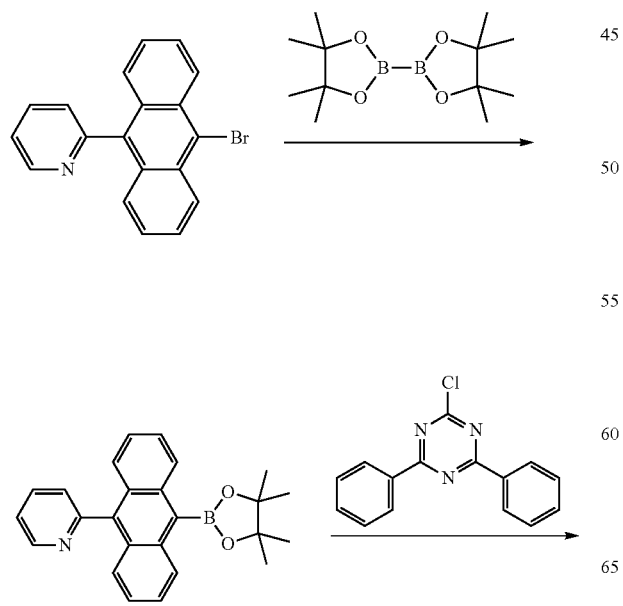

36

-continued

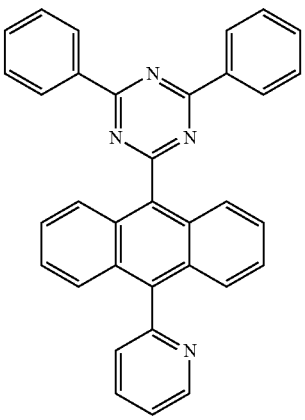

2-(10-(4,4,5,5-tetramethyl-1,3,2-dioxaborolan-2-yl)anthracen-9-yl)pyridine

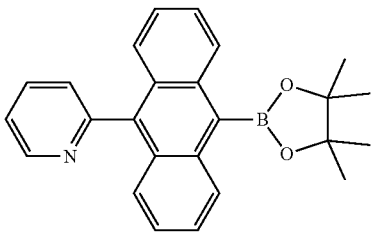 [SMILES: CC1(C)OB(c2c3ccccc3c(-c3ccccn3)c3ccccc23)OC1(C)C]

A flask was flushed with nitrogen and charged with 2-(10-bromoanthracen-9-yl)pyridine (17.2 g, 51.4 mmol), bis(pinacolato)diboron (14.3 g, 56.6 mmol), Pd(dppf)Cl$_2$ (2.2 g, 3.1 mmol), and potassium acetate (12.6 g, 128 mmol). Dry and deaerated DMF (230 mL) was added and the reaction mixture was heated to 80° C. under a nitrogen atmosphere for 4 days. Subsequently, all volatiles were removed in vacuo, water and dichloromethane were added and the organic phase was washed with water four times. After drying over MgSO$_4$, the organic phase was filtered over a Florisil/silica pad. After rinsing with additional dichloromethane, the colorless filtrate was filtrate was evaporated to dryness, and residue recrystallized from hexane. The resulting suspension was stirred for 1 h at room temperature and the solid was collected by suction filtration to yield 5 g (26%) of solid after drying. HPLC: 98.4%.

37

2,4-diphenyl-6-(10-(pyridin-2-yl)anthracen-9-yl)-1,3,5-triazine

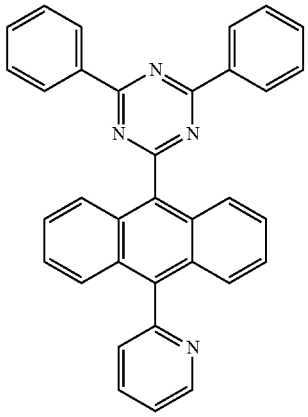

A flask was flushed with nitrogen and charged with 2-chloro-4,6-diphenyl-1,3,5-triazine (3.3 g, 12.4 mmol), 2-(10-(4,4,5,5-tetramethyl-1,3,2-dioxaborolan-2-yl)anthracen-9-yl)pyridine (5.0 g, 13.1 mmol), Pd(PPh$_3$)$_4$ (0.43 g, 0.37 mmol), and K$_2$CO$_3$ (5.2 g, 37.4 mmol). A mixture of deaerated 1,4-dioxane/water (3.5:1, 85 mL) was added and the reaction mixture was heated to 90° C. under a nitrogen atmosphere for 16 h. After cooling down to room temperature, the resulting precipitate was isolated by suction filtration and washed with 1,4-dioxane, water, and methanol. The obtained grey solid was dissolved in dichloromethane, the organic phase dried over MgSO$_4$, and filtered over a pad of Florisil. After rinsing with additional dichloromethane, the colorless filtrate was evaporated to dryness, and the residue recrystallized from chlorobenzene. The resulting precipitate was isolated by suction filtration and washed with hexane to yield 3.8 g (62%) of a yellow solid after drying. Final purification was achieved by sublimation. HPLC/ESI-MS: 100%, m/z=487 ([M+H]$^+$).

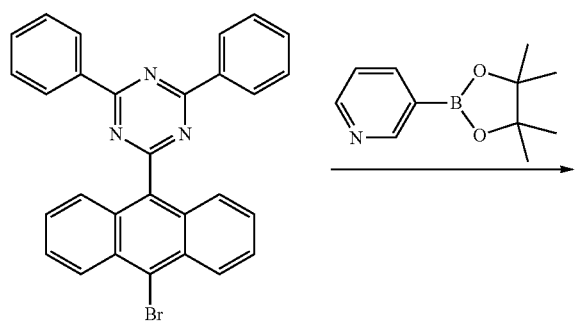

38

-continued

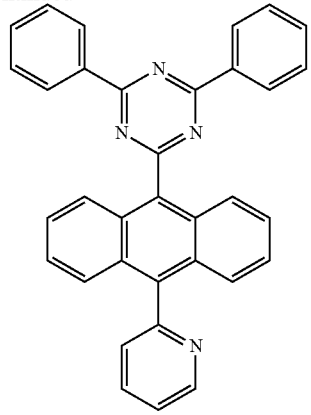 [SMILES: c1ccc(-c2nc(-c3ccccc3)nc(-c3c4ccccc4c(-c4ccccn4)c4ccccc34)n2)cc1]

2,4-diphenyl-6-(10-(pyridin-3-yl)anthracen-9-yl)-1,3,5-triazine

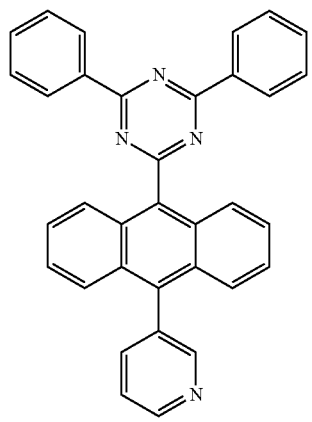 [SMILES: c1ccc(-c2nc(-c3ccccc3)nc(-c3c4ccccc4c(-c4cccnc4)c4ccccc34)n2)cc1]

A flask was flushed with nitrogen and charged with 2-(10-bromoanthracen-9-yl)-4,6-diphenyl-1,3,5-triazine (9.5 g, 19.5 mmol), 3-(4,4,5,5-tetramethyl-1,3,2-dioxaborolan-2-yl)pyridine (32.3 g, 157.7 mmol), Pd(dppf)Cl$_2$ (1.4 g, 1.9 mmol), tetra-N-butylammonium bromide (0.63 g, 1.95 mmol) and K$_2$CO$_3$ (26.8 g, 194.1 mmol). A mixture of deaerated THF/water (4:1, 275 mL) was added and the reaction mixture was heated to 75° C. under a nitrogen atmosphere for in total 12 days. After cooling down to room temperature, all volatiles were removed in vacuo. The residual solid was dissolved in dichloromethane/water and the organic phase was washed with water (until pH neutral). The organic phase was dried over Na$_2$SO$_4$, filtered and evaporated to dryness. Purification was achieved by column chromatography (silica, dichloromethane). After drying, 6.5 g (68%) of a yellow solid were obtained. Final purification was achieved by sublimation. HPLC/ESI-MS: 100%, m/z=487 ([M+H]$^+$).

General Procedure for Fabrication of Organic Electronic Devices

In general organic electronic devices may be organic light-emitting diodes (OLEDs), organic photovoltaic cells (OSCs), organic field-effect transistors (OFETs) or organic light emitting transistors (OLETs). Organic electronic light-emitting devices such as OLED and OLET may be part of a lighting device.

Any functional layer in the organic electronic device may comprise a compound of formula 1 or may consist of a compound of formula 1.

An OLED may be composed of individual functional layers to form a top-emission OLED which emits light through the top electrode. Herein, the sequence of the individual functional layers may be as follows wherein contact interfaces between the individual layers are shown as "/": non-transparent anode layer (bottom electrode)/hole injection layer/hole transport layer/electron blocking layer/ emission layer/hole blocking layer/electron transport layer/ electron injection layer/transparent cathode layer (top electrode). Each layer may in itself be constituted by several sub-layers.

An OLED may be composed of individual functional layers to form a bottom-emission OLED which emits light through the bottom electrode. Herein, the sequence of the individual functional layers may be as follows wherein contact interfaces between the individual layers are shown as "/": transparent anode layer (bottom electrode)/hole injection layer/hole transport layer/electron blocking layer/emission layer/hole blocking layer/electron transport layer/electron injection layer/non-transparent cathode layer (top electrode). Each layer may in itself be constituted by several sub-layers.

Top-emission OLED devices were prepared to demonstrate the technical benefit utilizing the compounds of formula 1 in an organic electronic device.

Fabrication of Top Emission OLED Devices

For all top emission devices, inventive examples 1 to 7 and comparative examples to 3, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode. 100 nm Ag were deposited at a pressure of 10-5 to 10-mbar to form the anode. Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 4,4',4''-((1E,1'E,1''E)-cyclopropane-1,2,3-triylidenetris(cyanomethanylylidene))tris(2,3,5,6-tetrafluorobenzonitrile) was vacuum deposited on the Ag electrode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine (CAS 1242056-42-3) was vacuum deposited on the HIL, to form a HTL having a thickness of 118 nm. Then, N,N-bis(4-(dibenzo[b,d]furan-4-yl)phenyl)-[1,1':4',1''-terphenyl]-4-amine (CAS 1198399-61-9) was vacuum deposited on the HTL, to form an electron blocking layer (EBL) having a thickness of 5 nm.

Subsequently, 97 vol.-% H06 (Sun Fine Chemicals) as EML host and 3 vol.-% BD200 (Sun Fine Chemicals) as fluorescent blue dopant were deposited on the EBL, to form a blue-emitting EML with a thickness of 20 nm. Then, the hole blocking layer is formed with a thickness of 5 nm by depositing 2,4-diphenyl-6-(4',5',6'-triphenyl-[1,1'2',1'':3'', 1''':3''',1''''-quinquephenyl]-3''''-yl)-1,3,5-triazine on the emission layer. Then, the electron transporting layer is formed on the hole blocking layer according to inventive example 1 to 7 and comparative examples 1 to 3 with a the thickness of 31 nm. The electron transport layer comprises compounds of formula 1 (or of the comparative compound) and an alkali metal compound, according to table 3.

Then, for all top emission devices Ag is evaporated at a rate of 0.01 to 1 Å/s at 10-mbar to form a cathode with a thickness of 11 nm. A cap layer of Biphenyl-4-yl(9,9-diphenyl-9H-fluoren-2-yl)-[4-(9-phenyl-9H-carbazol-3-yl) phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the existing art, the light output of the top emission OLEDs is measured under ambient conditions (20° C.). Current voltage measurements are performed using a Keithley 2400 sourcemeter, and recorded in V. At 10 mA/cm$^2$ for top emission devices, a spectrometer CAS140 CT from Instrument Systems, which has been calibrated by Deutsche Akkreditierungsstelle (DAkkS), is used for measurement of CIE coordinates and brightness in Candela. The current efficiency Ceff is determined at 10 mA/cm in cd/A.

In top emission devices, the emission is forward directed, non-Lambertian and also highly dependent on the microcavity. Therefore, the external quantum efficiency (EQE) and power efficiency in lm/W will be higher compared to bottom emission devices.

Compounds Used

| IUPAC name | Reference |
| --- | --- |
| Biphenyl-4-yl(9,9-diphenyl-9H-fluoren-2-yl)-[4-(9-phenyl-9H-carbazol-3-yl)phenyl]-amine (CAS 1242056-42-3) | US2016322581 |
| 4,4',4''-((1E,1'E,1''E)-cyclopropane-1,2,3-triylidenetris(cyanomethanylylidene))tris(2,3,5,6-tetrafluorobenzonitrile) | US2008265216 |
| N,N-bis(4-(dibenzo[b,d]furan-4-yl)phenyl)-[1,1':4',1''-terphenyl]-4-amine (CAS 1198399-61-9) | JP2014096418 |
| Ho6 (Fluorescent-blue host material) | Commercially available from Sun Fine Chemicals, Inc, S. Korea |
| BD200 (Fluorescent-blue emitter material) | Commercially available from Sun Fine Chemicals, Inc, S. Korea |
| 2,4-diphenyl-6-(4',5',6'-triphenyl-[1,1':2',1'':3'',1''':3''',1''''-quinquephenyl]-3''''-yl)-1,3,5-triazine | — |
| 8-Hydroxyquinolinolato-lithium (CAS 850918-68-2) = AMC-1 = LiQ | WO2013079217 |
| Lithium tetra(1H-pyrazol-1-yl)borate = AMC-2 | US20140332789 |
| Lithium 2-(diphenylphosphoryl)phenolate = AMC-3 | US20140353649 |

Melting Point

The melting point (Tm) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 µL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Rate Onset Temperature

The rate onset temperature ($T_{RO}$) for transfer into the gas phase is determined by loading 100 mg compound into a VTE source. As WE source a point source for organic materials is used as supplied by Kurt J. Lesker Company (www.lesker.com) or CreaPhys GmbH (http://www.creaphys.com). The VTE (vacuum thermal evaporation) source temperature is determined through a thermocouple in direct contact with the compound in the VTE source.

The VTE source is heated at a constant rate of 15 K/min at a pressure of $10^{-7}$ to $10^{-8}$ mbar in the vacuum chamber and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate on a logarithmic scale is plotted against the VTE source temperature. The rate onset is the temperature at which noticeable deposition on the QCM detector occurs (defined as a rate of 0.02 Å/s. The VTE source is heated and cooled three time and only results from the second and third run are used to determine the rate onset temperature. The rate onset temperature is an indirect measure of the volatility of a compound. The higher the rate onset temperature the lower is the volatility of a compound.

Technical Effect of the Invention

Material Property

The Tg of compounds of formula 1(Table 2) are significantly increased versus the compounds of existing art (Table 1). The values are in a range suitable for use in organic electronic devices. High Tg values of materials used in organic electronics are generally preferred for device durability and robustness.

Top Emission Devices

Surprisingly, the cd/A current efficiencies of top emission OLED devices enhanced when using a combination of compounds of formula 1 with alkali metal compounds as an electron transport layer In Table 3 is shown the performance of in organic electronic device comprising an organic semiconducting layer comprising a compound of formula 1 and an alkali metal compound (AMC). Three different types of alkali metal compounds were tested, as specified in the overview of compounds used.

In summary, improved cd/A efficiency may be achieved when the electron transporting organic semiconducting layer comprises a compound of formula 1. High performance may be achieved for a range of alkali metal compounds.

In summary, organic electronic devices comprising compounds with formula 1 inherent to their molecular structure have higher current efficiency. The glass transition temperature and rate onset temperature are within the range acceptable for mass production of organic semiconducting layers.

TABLE 1

Structural formulae, glass transition temperatures, melting temperatures, rate onset temperatures of comparative compounds.

| | Name | Formula | Tg [° C.] | Tm [° C.] | $T_{RO}$ [° C.] |
|---|---|---|---|---|---|
| Comparative Compound 1 | Comparative-1 | 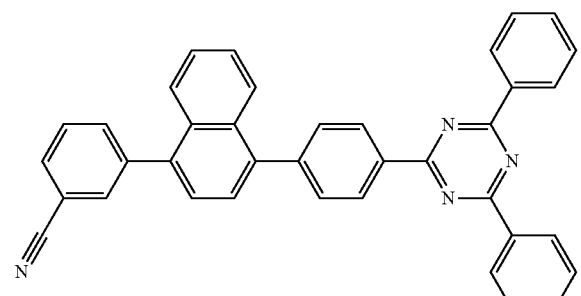 | 99 | 252 | 216 |
| Comparative compound 2 | Comparative-2 | 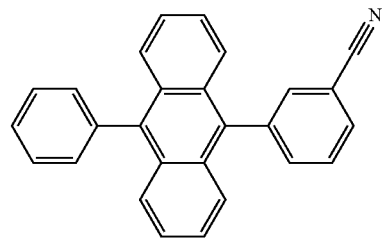 [SMILES: N#Cc1cccc(-c2c3ccccc3c(-c3ccccc3)c3ccccc23)c1] | 71 | 233 | 139 |

TABLE 2

Structural formulae, glass transition temperatures, melting temperatures, rate onset temperatures of inventive compounds.

| Name | | Formula | Tg [° C.] | Tm [° C.] | $T_{RO}$ [° C.] |
|---|---|---|---|---|---|
| Inventive Compound 1 | (N) | | 137 | 329 | 244 |
| Inventive compound 2 | (J) | | 141 | 296 | 248 |
| Inventive Compound 3 | (E) | | 146 | 334 | 256 |
| Inventive Compound 4 | (F) | | 147 | 330 | 263 |

In Table 1 are shown glass transition temperatures, melting temperatures, rate onset temperatures of comparative compounds.

In Table 2 are shown glass transition temperatures, melting temperatures, rate onset temperatures of compounds of formula 1.

TABLE 3

Performance data of top emission OLED devices comprising an electron transport layer, which comprises the compounds of formula 1 and comparative compounds and an alkali metal compound (AMC). The inventive examples show increased cd/A efficiencies Ceff.

| | Comparative compounds and compounds of formula 1 | vol.-% compound of formula 1 | Alkali metal compound (AMC) | vol.-% alkali metal compound | Total Thickness ETL/nm | CIE 1931 y | Operating voltage at 10 mA/cm² (V) | cd/A efficiency Ceff at 10 mA/cm² (cd/A) |
|---|---|---|---|---|---|---|---|---|
| Comparative example 1 | Comparative-1 | 50 | AMC-1 | 50 | 31 | 0.044 | 3.59 | 7.6 |
| Comparative example 2 | Comparative-1 | 70 | AMC-2 | 30 | 31 | 0.044 | 3.68 | 7.4 |
| Comparative example 3 | Comparative-2 | 70 | AMC-2 | 30 | 31 | 0.046 | 3.49 | 7.6 |
| Inventive example 1 | N | 50 | AMC-1 | 50 | 31 | 0.048 | 3.42 | 8.0 |
| Inventive example 2 | N | 50 | AMC-3 | 50 | 31 | 0.047 | 3.42 | 7.9 |
| Inventive example 3 | J | 50 | AMC-1 | 50 | 31 | 0.052 | 3.44 | 8.1 |
| Inventive example 4 | J | 70 | AMC-2 | 30 | 31 | 0.050 | 3.64 | 7.9 |
| Inventive example 5 | E | 50 | AMC-1 | 50 | 31 | 0.048 | 3.42 | 7.9 |
| Inventive example 6 | F | 50 | AMC-1 | 50 | 31 | 0.050 | 3.46 | 8.3 |
| Inventive example 7 | F | 70 | AMC-2 | 30 | 31 | 0.050 | 3.54 | 8.3 |

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The features disclosed in the foregoing description and in the claims may, both separately or in any combination, be material for realizing the invention in diverse forms thereof.

The invention claimed is:

1. A compound represented by the general formula (I):

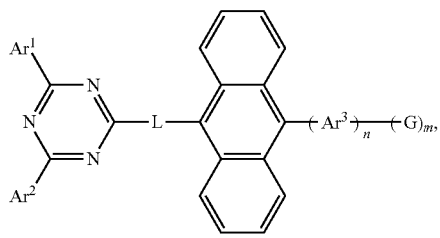

wherein $Ar^1$ and $Ar^2$ are independently selected from the group consisting of substituted or unsubstituted $C_6$ to $C_{60}$ aryl and substituted or unsubstituted $C_2$ to $C_{60}$ heteroaryl, wherein the substituents, if present in the respective aryl or heteroaryl group, are independently selected from the group consisting of $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched fluorinated cyclic alkyl, $C_3$-$C_{12}$ fluorinated cyclic alkyl, $C_3$-$C_{12}$ fluorinated cyclic alkoxy; CN; $C_2$-$C_{20}$ heteroaryl, OR, SR, (C=O)R, (C=O)$NR_2$, $SiR_3$, (S=O)R, (S=O)$_2$R, $C_{12}$-$C_{40}$ aryl phosphine oxide, $C_7$-$C_{40}$ aryl-alkyl-phosphine oxide;

$Ar^3$ is selected from the group consisting of substituted or unsubstituted $C_6$ to $C_{60}$ arylene, wherein the substitutents, if present in the arylene group, are independently selected from the group consisting of $C_1$-$C_{20}$ linear alkyl, $C_3$-$C_{20}$ branched alkyl, $C_3$-$C_{20}$ cyclic alkyl; $C_1$-$C_{20}$ linear alkoxy, $C_3$-$C_{20}$ branched alkoxy; linear fluorinated $C_1$-$C_{12}$ alkyl, or linear fluorinated $C_1$-$C_{12}$ alkoxy; $C_3$-$C_{12}$ branched fluorinated cyclic alkyl, $C_3$-$C_{12}$ fluorinated cyclic alkyl, $C_3$-$C_{12}$ fluorinated cyclic alkoxy; CN; $C_2$-$C_{20}$ heteroaryl, OR, SR, (C=O)R, (C=O)$NR_2$, $SiR_3$, (S=O)R, (S=O)$_2$R, $C_{12}$-$C_{40}$ aryl phosphine oxide, $C_7$-$C_{40}$ aryl-alkyl-phosphine oxide;

L is selected from $C_6$ to $C_{60}$ arylene;

n is 0 or 1;

m is an integer from 1 to 3;

G is selected from the group consisting of CN and substituted or unsubstituted pyridinyl, wherein the substituents, if present, are independently selected from the group consisting of $C_1$ to $C_{20}$ linear alkyl, $C_3$ to $C_{20}$ branched alkyl, and $C_3$ to $C_{20}$ cyclic alkyl; and R is independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl.

2. The compound according to claim 1, wherein $Ar^1$ and $Ar^2$ are independently selected from unsubstituted $C_6$ to $C_{60}$ aryl or $C_2$ to $C_{60}$ heteroaryl.

3. The compound according to claim 1, wherein L is substituted or unsubstituted $C_6$ arylene.

4. The compound according to claim 1, wherein $Ar^1$ and $Ar^2$ are independently selected from unsubstituted $C_6$ to $C_{42}$ aryl or $C_2$ to $C_{42}$ heteroaryl; $Ar^3$ is selected from unsubstituted $C_6$ to $C_{42}$ arylene; L is $C_6$ to $C_{42}$ arylene; G is substituted or unsubstituted pyridinyl or CN, n is 0 or 1; and m is 1.

5. The compound according to claim 4, wherein Ar¹ and Ar² are independently selected from phenyl, biphenyl, naphtyl, dibenzofuranyl, fluorenyl, or dibenzothionyl; Ar³, if present, is phenyl; L is phenyl; G is substituted or unsubstituted pyridinyl or CN.
6. The compound according to claim 1, represented by one of the following formulas A to J or M:
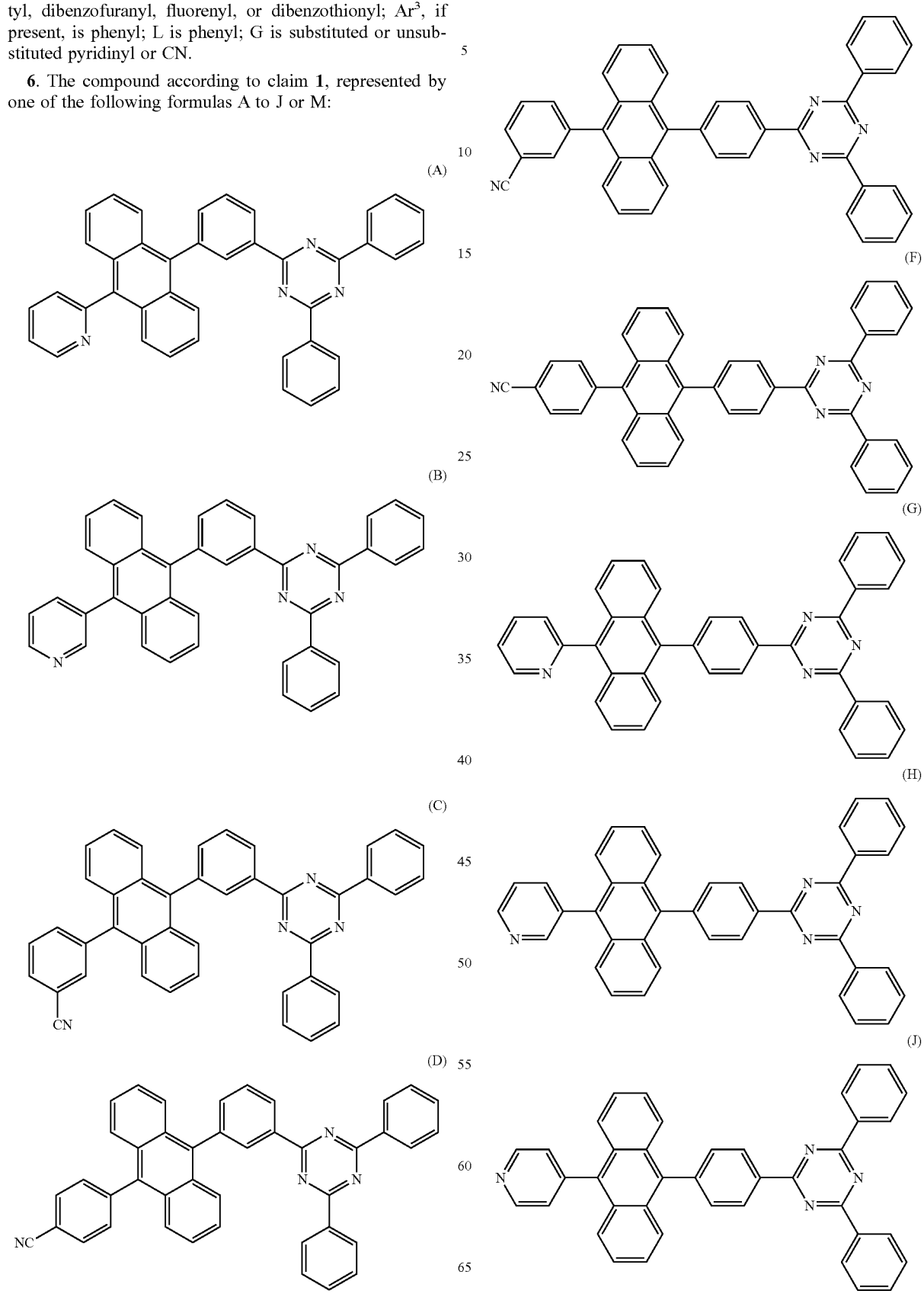

-continued

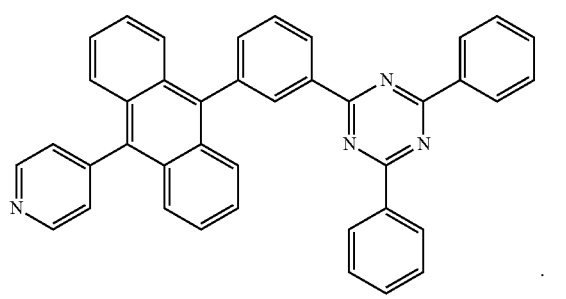
(M)

7. An organic semiconducting layer comprising the compound according to claim 1.

8. The organic semiconducting layer according to claim 7, further comprising an additive selected from the group consisting of metal, metal salt, and organic metal complex.

9. The organic semiconducting layer according to claim 8, wherein the additive is 8-hydroxyquinolinatolithium or Lithium tetra(1H-pyrazol-1-yl)borate.

10. An organic electronic device comprising, between an anode and a cathode and in electrical contact with the anode and the cathode, the organic semiconducting layer according to claim 7.

11. The organic electronic device according to claim 10, further comprising an emission layer, wherein the organic semiconducting layer is arranged between the emission layer and the cathode.

12. The device comprising the organic electronic device according to claim 10, the device being a display device or a lighting device.

* * * * *